US012697412B2

(12) United States Patent
Johnson et al.

(10) Patent No.: US 12,697,412 B2
(45) Date of Patent: Aug. 4, 2026

(54) MATERIALS FOR PIEZOELECTRIC IMPLANTS, AND METHODS OF POLING MATERIALS FOR PIEZOELECTRIC RESPONSE FOR BONE GROWTH STIMULATION

(71) Applicant: DMJ Concepts, LLC, Louisville, KY (US)

(72) Inventors: John Robert Johnson, Louisville, KY (US); Kimathi Doss, Louisville, KY (US)

(73) Assignee: DMJ Concepts, LLC, Louisville, KY (US)

( * ) Notice: Subject to any disclaimer, the term of this patent is extended or adjusted under 35 U.S.C. 154(b) by 434 days.

(21) Appl. No.: 18/241,618

(22) Filed: Sep. 1, 2023

(65) Prior Publication Data

US 2024/0058504 A1     Feb. 22, 2024

Related U.S. Application Data

(63) Continuation of application No. PCT/US2022/018736, filed on Mar. 3, 2022.

(60) Provisional application No. 63/299,540, filed on Jan. 14, 2022, provisional application No. 63/243,901, filed on Sep. 14, 2021, provisional application No.
(Continued)

(51) Int. Cl.
| | |
|---|---|
| A61F 2/44 | (2006.01) |
| A61F 2/30 | (2006.01) |
| A61L 27/06 | (2006.01) |
| A61L 27/18 | (2006.01) |
| A61L 27/50 | (2006.01) |

(52) U.S. Cl.
CPC .......... *A61L 27/06* (2013.01); *A61F 2/30771* (2013.01); *A61F 2/447* (2013.01); *A61L 27/18* (2013.01); *A61L 27/50* (2013.01); *A61F 2002/30785* (2013.01); *A61L 2430/38* (2013.01)

(58) Field of Classification Search
CPC ........ A61F 2/442; A61F 2/4455; A61F 2/447; A61L 27/06
USPC ........................................... 623/17.11–17.16
See application file for complete search history.

(56) References Cited

U.S. PATENT DOCUMENTS

| | | | |
|---|---|---|---|
| 6,858,551 B1* | 2/2005 | Turkevich | C08K 3/10 128/205.27 |
| 9,484,524 B2 | 11/2016 | Yu et al. | |
| 2011/0118852 A1 | 5/2011 | Evans | |

(Continued)

FOREIGN PATENT DOCUMENTS

WO     WO-20190180586 A1     9/2019

OTHER PUBLICATIONS

PCT International Search Report and Written Opinion for PCT/US2022/018736 that is a parent application to the instant application; Jun. 15, 2022; 7 pages.

(Continued)

*Primary Examiner* — Eduardo C Robert
*Assistant Examiner* — Christina Negrellirodriguez
(74) *Attorney, Agent, or Firm* — Harness, Dickey & Pierce, P.L.C.; Anthony G. Fussner

(57)     ABSTRACT

Disclosed are exemplary embodiments of materials for piezoelectric implants. Also disclosed are exemplary methods of poling materials for piezoelectric response for bone
(Continued)

growth stimulation. Additional exemplary embodiments are disclosed of piezoelectric implants comprising such materials.

20 Claims, 21 Drawing Sheets

Related U.S. Application Data

63/196,137, filed on Jun. 2, 2021, provisional application No. 63/156,192, filed on Mar. 3, 2021.

(56) References Cited

U.S. PATENT DOCUMENTS

| | | | |
|---|---|---|---|
| 2015/0134061 A1* | 5/2015 | Friis | B29C 45/0001 |
| | | | 264/439 |
| 2015/0238655 A1* | 8/2015 | Jongpaiboonkit | ........................... A61K 38/1875 |
| | | | 424/602 |
| 2019/0334078 A1 | 10/2019 | Araujo Da Silva et al. | |
| 2019/0365541 A1 | 12/2019 | Friis et al. | |
| 2021/0145598 A1* | 5/2021 | Klimek | A61F 2/4455 |
| 2022/0158075 A1* | 5/2022 | Khaliq | H10N 30/092 |
| 2022/0181543 A1* | 6/2022 | Guhathakurta | C08J 3/212 |

OTHER PUBLICATIONS

Technical Data Sheet; KetaSpire® KT-880; Solvay; Dec. 21, 2020; 7 pages.
Technical Data Sheet; FERRO, 2011; ferro.com; Jul. 2019; one page.

* cited by examiner

Piezo Elements

Titanium Coating

Peek Base

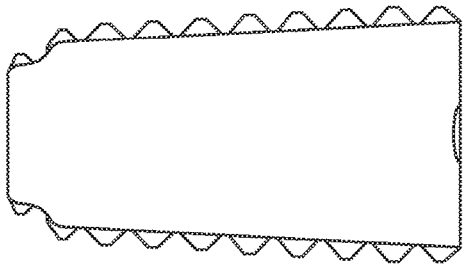
FIG. 20
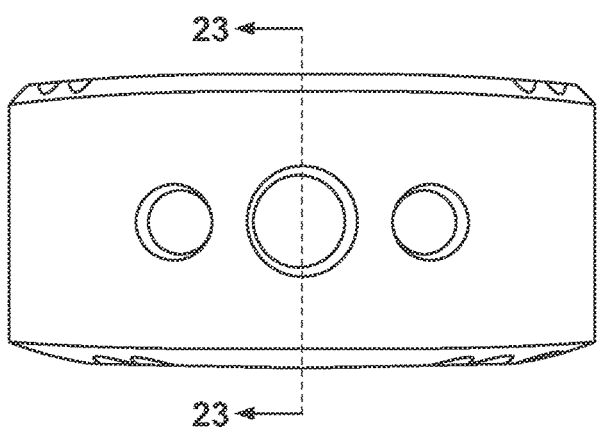
FIG. 21
FIG. 22

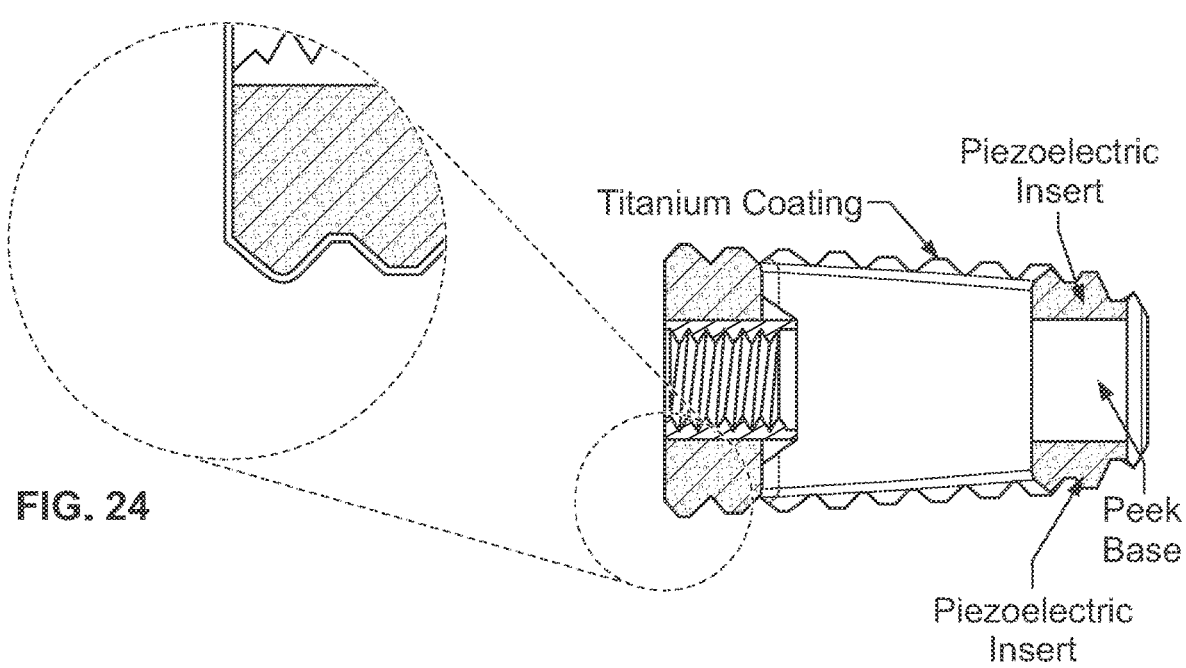
FIG. 24
FIG. 23
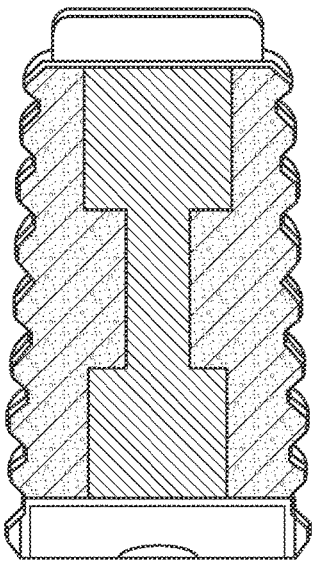
FIG. 25

Titanium
Coating

Piezoelectric
Insert

Peek
Base

Piezoelectric
Insert

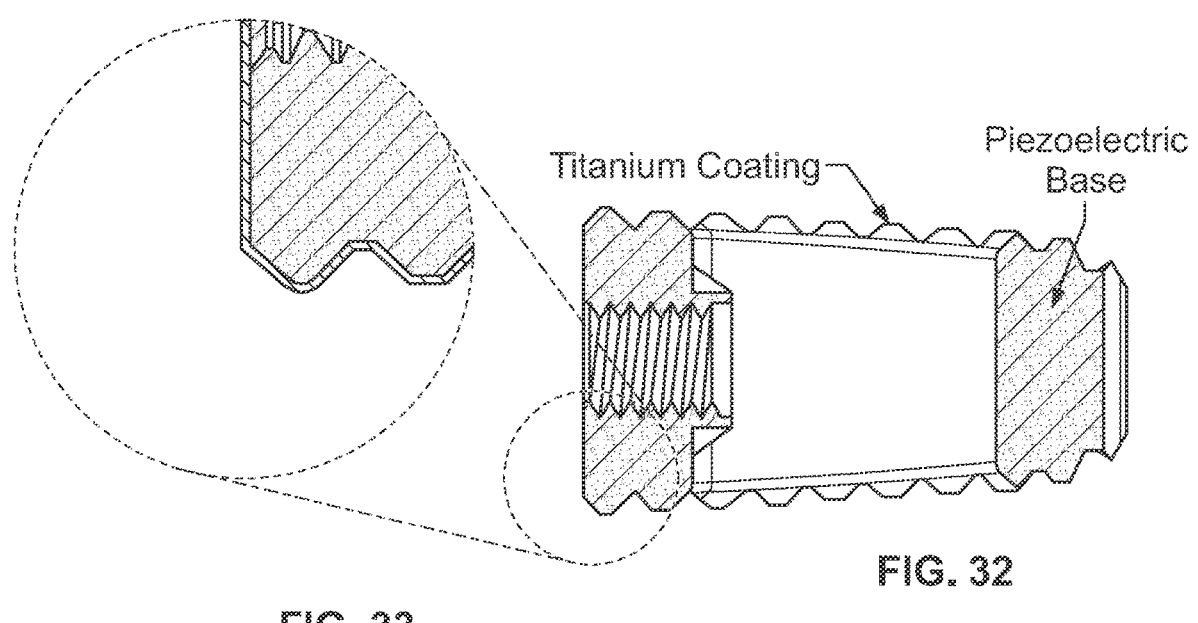
Titanium Coating
Piezoelectric Base
FIG. 33
FIG. 32
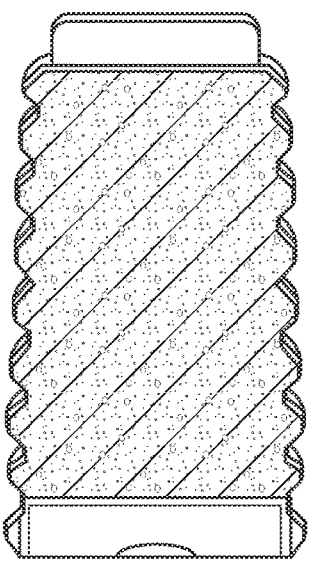
FIG. 34

Titanium
Coating

Piezoelectric
Base

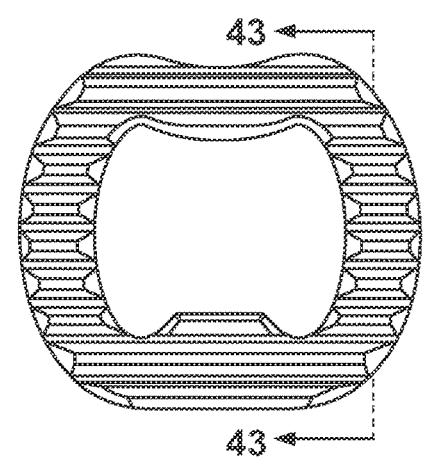
FIG. 40
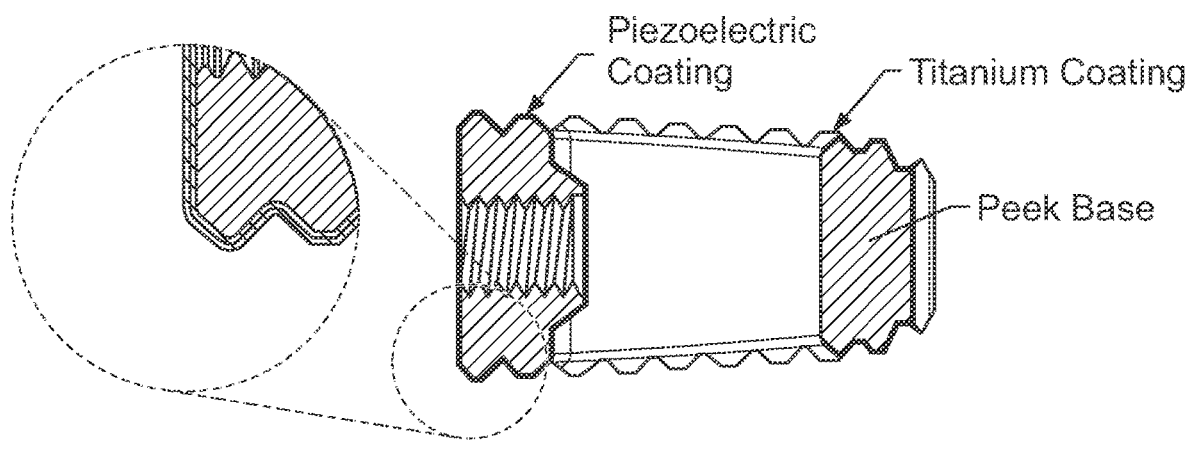
FIG. 42                    FIG. 41
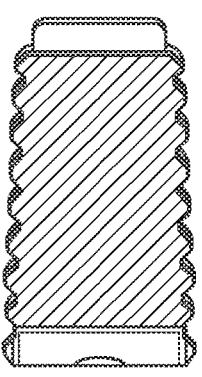
FIG. 43

Titanium
Coating

Piezoelectric
Coating

Peek Base

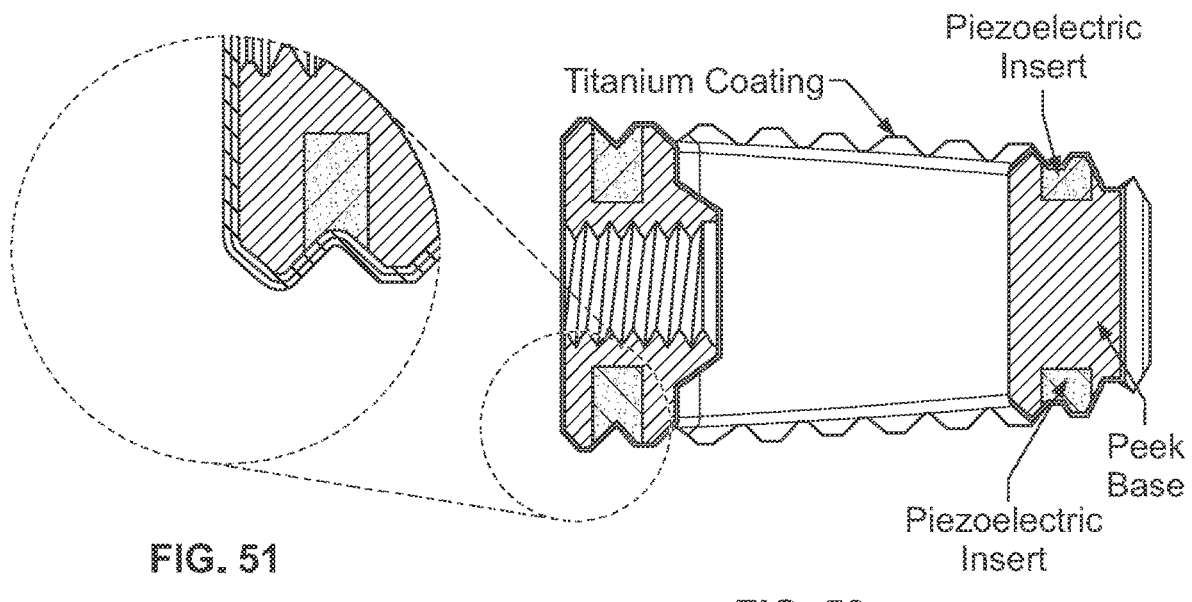
Titanium Coating
Piezoelectric Insert
Peek Base
Piezoelectric Insert
FIG. 51
FIG. 50
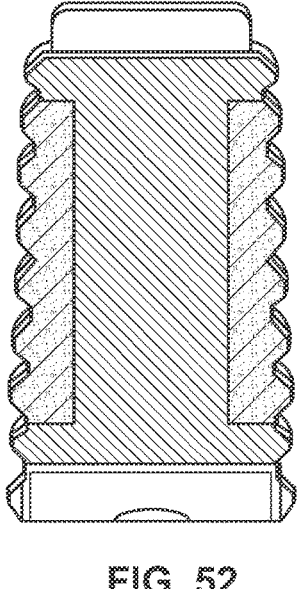
FIG. 52

Titanium
Coating

Piezoelectric
Insert

Peek
Base

Piezoelectric Insert

MATERIALS FOR PIEZOELECTRIC IMPLANTS, AND METHODS OF POLING MATERIALS FOR PIEZOELECTRIC RESPONSE FOR BONE GROWTH STIMULATION

CROSS-REFERENCE TO RELATED APPLICATIONS

This application is a continuation of PCT International Application No. PCT/US2022/018736 filed Mar. 3, 2022 (published as WO 2022/187509 on Sep. 9, 2022) which, in turn, claims priority to and the benefit of U.S. Provisional Patent Application No. 63/156,192 filed Mar. 3, 2021, U.S. Provisional Patent Application No. 63/196,137 filed Jun. 2, 2021, U.S. Provisional Patent Application No. 63/243,901 filed Sep. 14, 2021, and U.S. Provisional Patent Application No. 63/299,540 filed Jan. 14, 2022. The entire disclosures of these patent applications are incorporated herein by reference.

FIELD

The present disclosure relates to materials for piezoelectric implants. The present disclosure also relates to methods of poling for piezoelectric response for bone growth stimulation. The present disclosure further relates to piezoelectric implants comprising such materials.

BACKGROUND

This section provides background information related to the present disclosure which is not necessarily prior art.

Piezoelectric refers to the ability of certain materials to generate an electric charge in response to applied mechanical stress or pressure. For example, a piezoelectric spinal fusion implant will generate electricity to stimulate bone growth when the piezoelectric spinal fusion implant is subjected to applied stress and compressive loads during normal activities, such as walking, etc.

SUMMARY

This section provides a general summary of the disclosure and is not a comprehensive disclosure of its full scope or all of its features.

Disclosed are exemplary embodiments of materials for piezoelectric implants. Also disclosed are exemplary methods of poling materials for piezoelectric response for bone growth stimulation. Additional exemplary embodiments are disclosed of piezoelectric implants comprising such materials.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and is not intended to limit the scope of the present disclosure.

FIG. 1 is a perspective view of a material including barium titanate ($BaTiO_3$) and polyetheretherketone (PEEK)

according to an exemplary embodiment in which tunnels or closed-ended holes have been formed (e.g., drilled, etc.) in the $BaTiO_3$/PEEK material.

Figure 15:
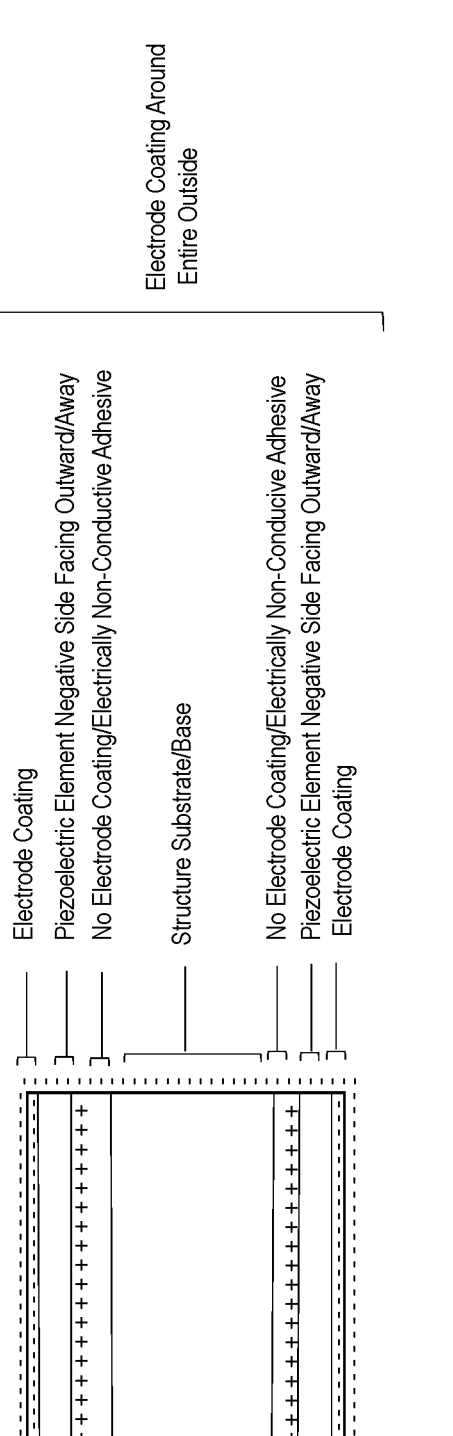
Figure 16:
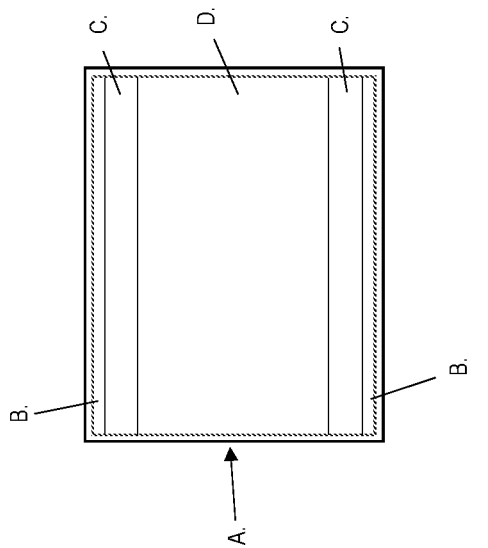

FIGS. 15 and 16 are cross-sectional views (not to scale) of a piezoelectric implant according to an exemplary embodiment including an electrode coating or shell (e.g., a titanium or other electrically-conductive coating provided via sputtering, plasma spraying, sol-gel, physical vapor deposition, or other suitable process, etc.) such that an entire outside of the piezoelectric implant has a negative charge as shown in FIG. 15.

Figure 17:
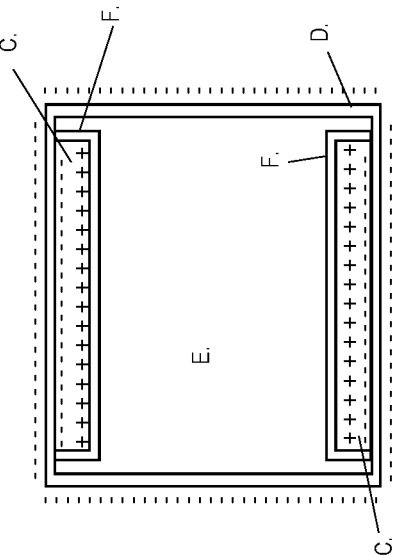

FIG. 17 is a cross-sectional views (not to scale) of a piezoelectric implant according to an exemplary embodiment including an electrically-conductive coating (e.g., a titanium or other electrically-conductive coating provided via sputtering, plasma spraying, sol-gel, physical vapor deposition, or other suitable process, etc.) such that an entire outside of the piezoelectric implant has a negative charge.

Figure 18:
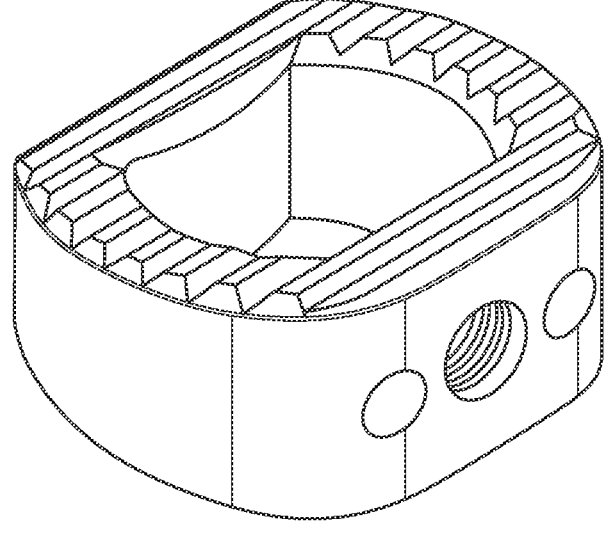
Figure 19:
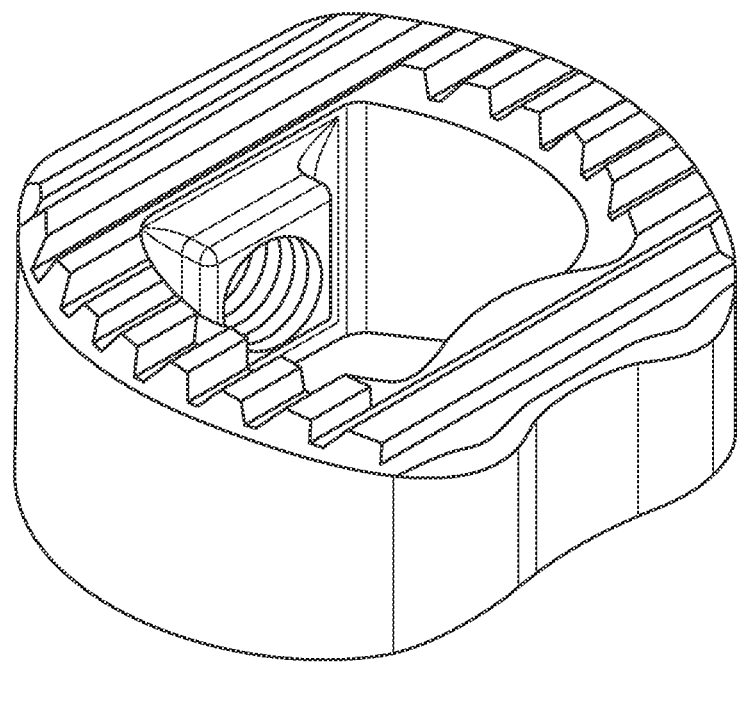

FIGS. 18 and 19 are perspective views of a piezoelectric implant (e.g., for use as a spinal fusion implant, etc.) according to an exemplary embodiment.

FIG. 20 is a side view of the piezoelectric implant shown in FIG. 18.

FIG. 21 is a front view of the piezoelectric implant shown in FIG. 18.

FIG. 22 is a top view of the piezoelectric implant shown in FIG. 18.

FIG. 23 is a cross-sectional view taken along the line 23-23 in FIG. 21.

FIG. 24 is a detailed view of the portion in FIG. 23 at a scale of 10:1.

FIG. 25 is a cross-sectional view taken along the line 25-25 in FIG. 22.

Figure 26:
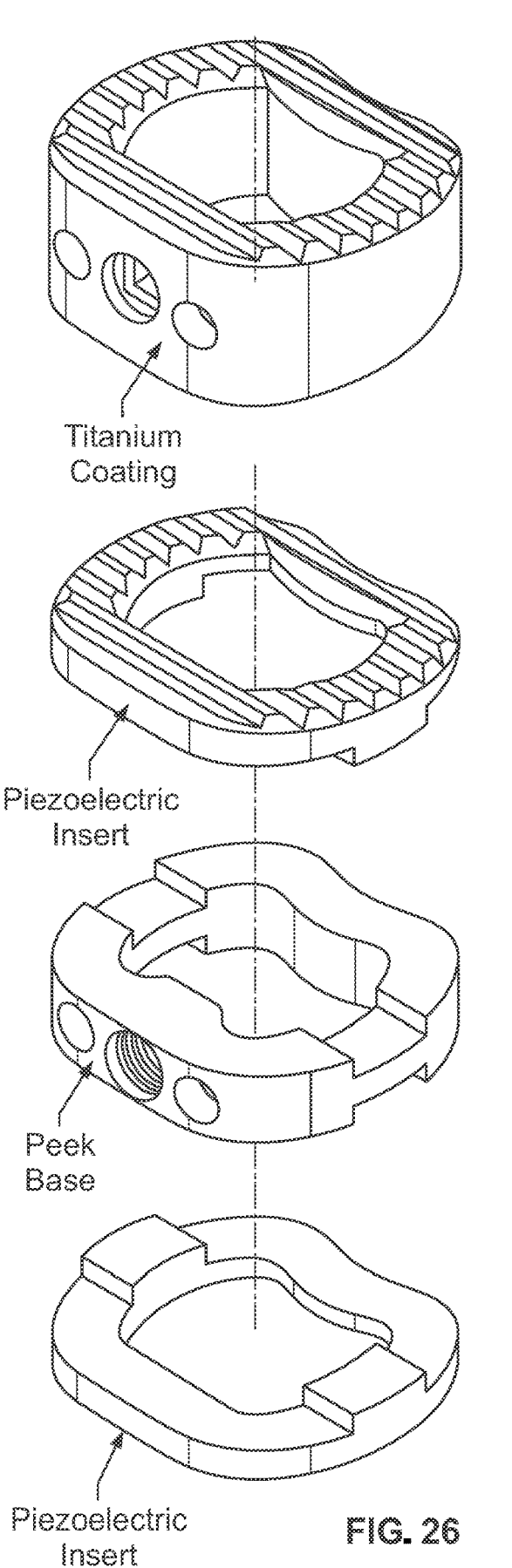

FIG. 26 is an exploded perspective view illustrating the electrically-conductive coating shown as a shell (e.g., a titanium or other electrically-conductive coating provided via sputtering, plasma spraying, sol-gel, physical vapor deposition, or other suitable process, etc.), the piezoelectric inserts (e.g., piezoelectric poled PVDF inserts, etc.) and base (e.g., PEEK base, etc.) of the piezoelectric implant shown in FIGS. 18-25. The electrically-conductive coating may be configured such that an entire outside of the piezoelectric implant has a negative charge.

Figure 27:
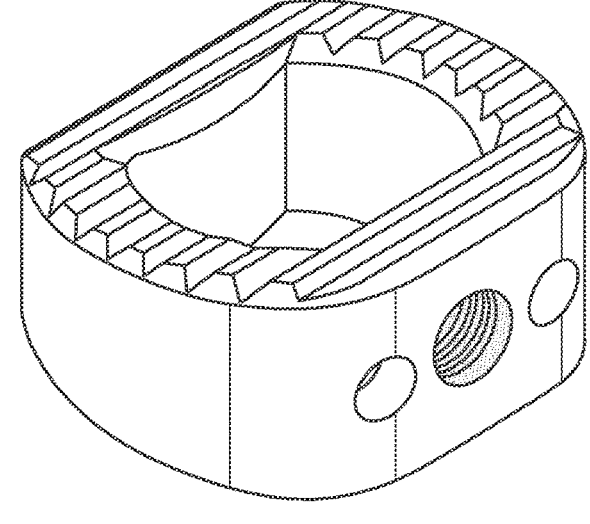
Figure 28:
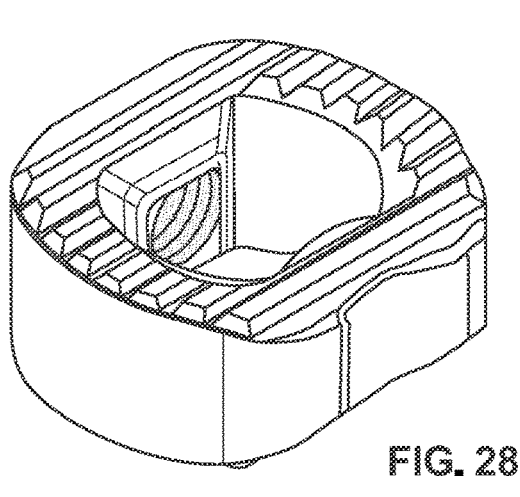

FIGS. 27 and 28 are perspective views of a piezoelectric implant (e.g., for use as a spinal fusion implant, etc.) according to an exemplary embodiment.

Figure 29:
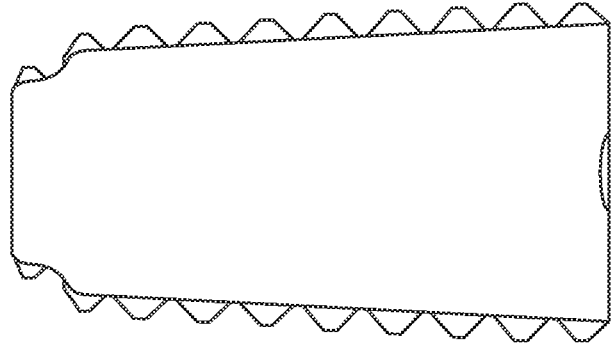

FIG. 29 is a side view of the piezoelectric implant shown in FIG. 27.

Figure 30:
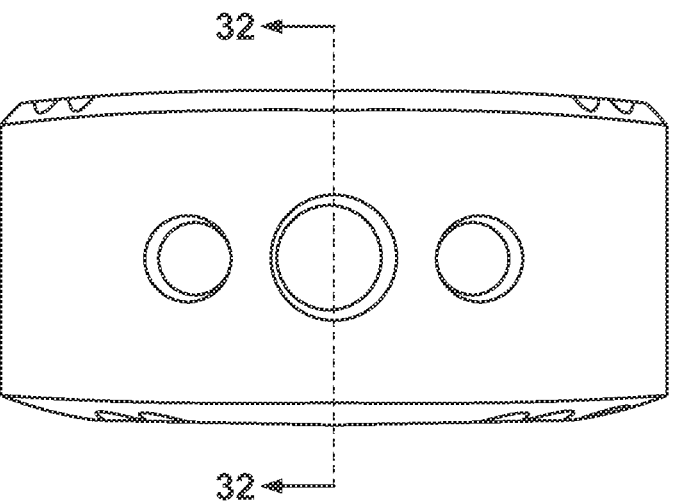

FIG. 30 is a front view of the piezoelectric implant shown in FIG. 27.

Figure 31:
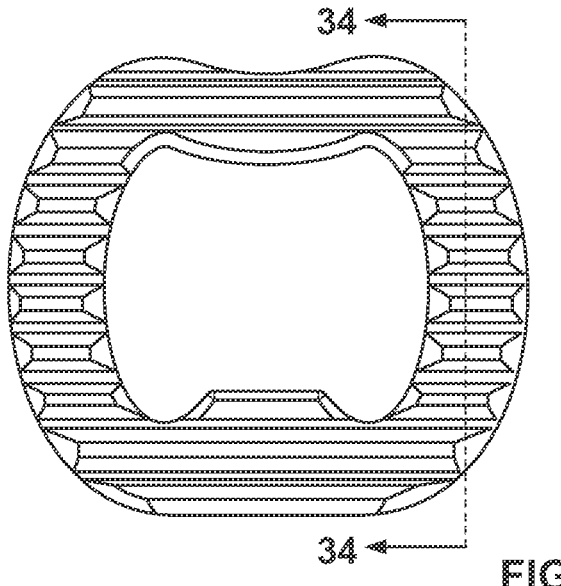

FIG. 31 is a top view of the piezoelectric implant shown in FIG. 27.

FIG. 32 is a cross-sectional view taken along the line 32-32 in FIG. 30.

FIG. 33 is a detailed view of the portion in FIG. 32 at a scale of 10:1.

FIG. 34 is a cross-sectional view taken along the line 34-34 in FIG. 31.

Figure 35:
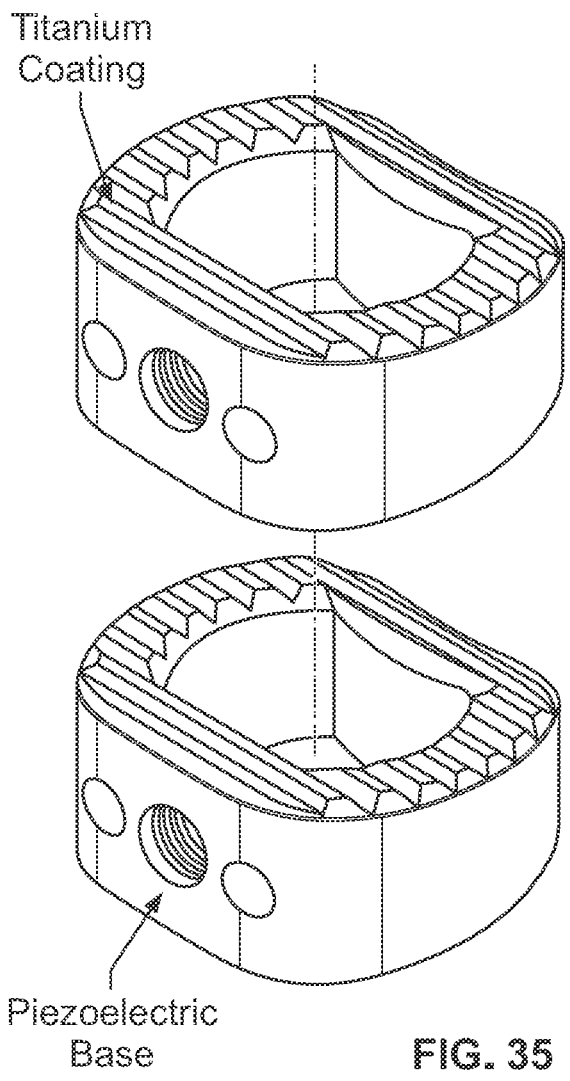

FIG. 35 is an exploded perspective view illustrating the electrically-conductive coating shown as a shell (e.g., a titanium or other electrically-conductive coating provided via sputtering, plasma spraying, sol-gel, physical vapor deposition, or other suitable process, etc.) and the piezo-electric base (e.g., piezoelectric poled PVDF base, etc.) of the piezoelectric implant shown in FIGS. 27-34. The electrically-conductive coating may be configured such that an entire outside of the piezoelectric implant has a negative charge.

Figure 36:
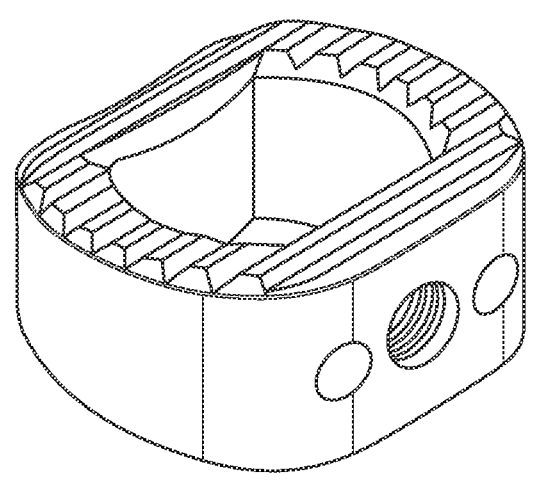
Figure 37:
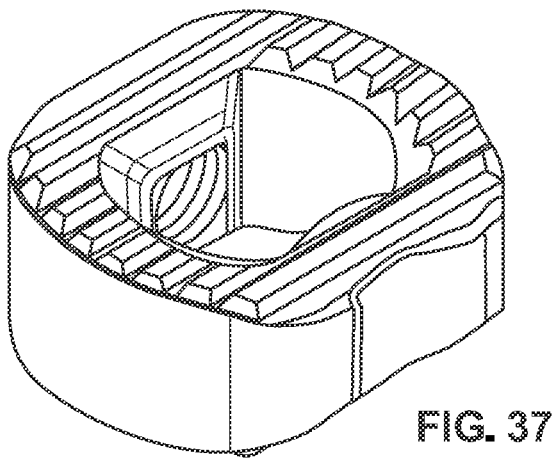

FIGS. 36 and 37 are perspective views of a piezoelectric implant (e.g., for use as a spinal fusion implant, etc.) according to an exemplary embodiment.

Figure 38:
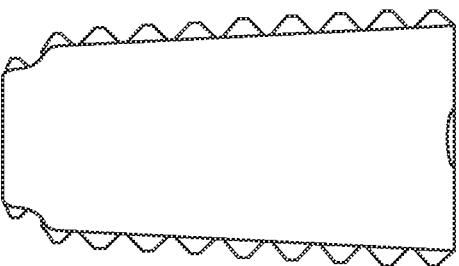

FIG. 38 is a side view of the piezoelectric implant shown in FIG. 36.

Figure 39:
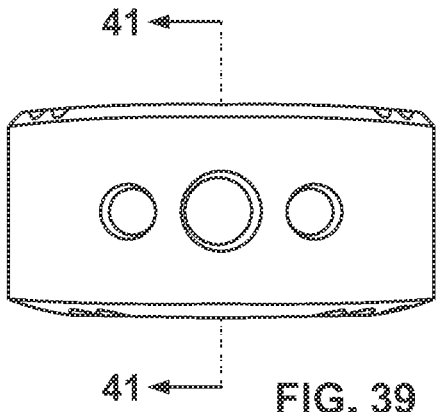

FIG. 39 is a front view of the piezoelectric implant shown in FIG. 36.

FIG. 40 is a top view of the piezoelectric implant shown in FIG. 36.

FIG. 41 is a cross-sectional view taken along the line 41-41 in FIG. 39.

FIG. 42 is a detailed view of the portion in FIG. 41 at a scale of 10:1.

FIG. 43 is a cross-sectional view taken along the line 43-43 in FIG. 40.

Figures 44, 45, 46:
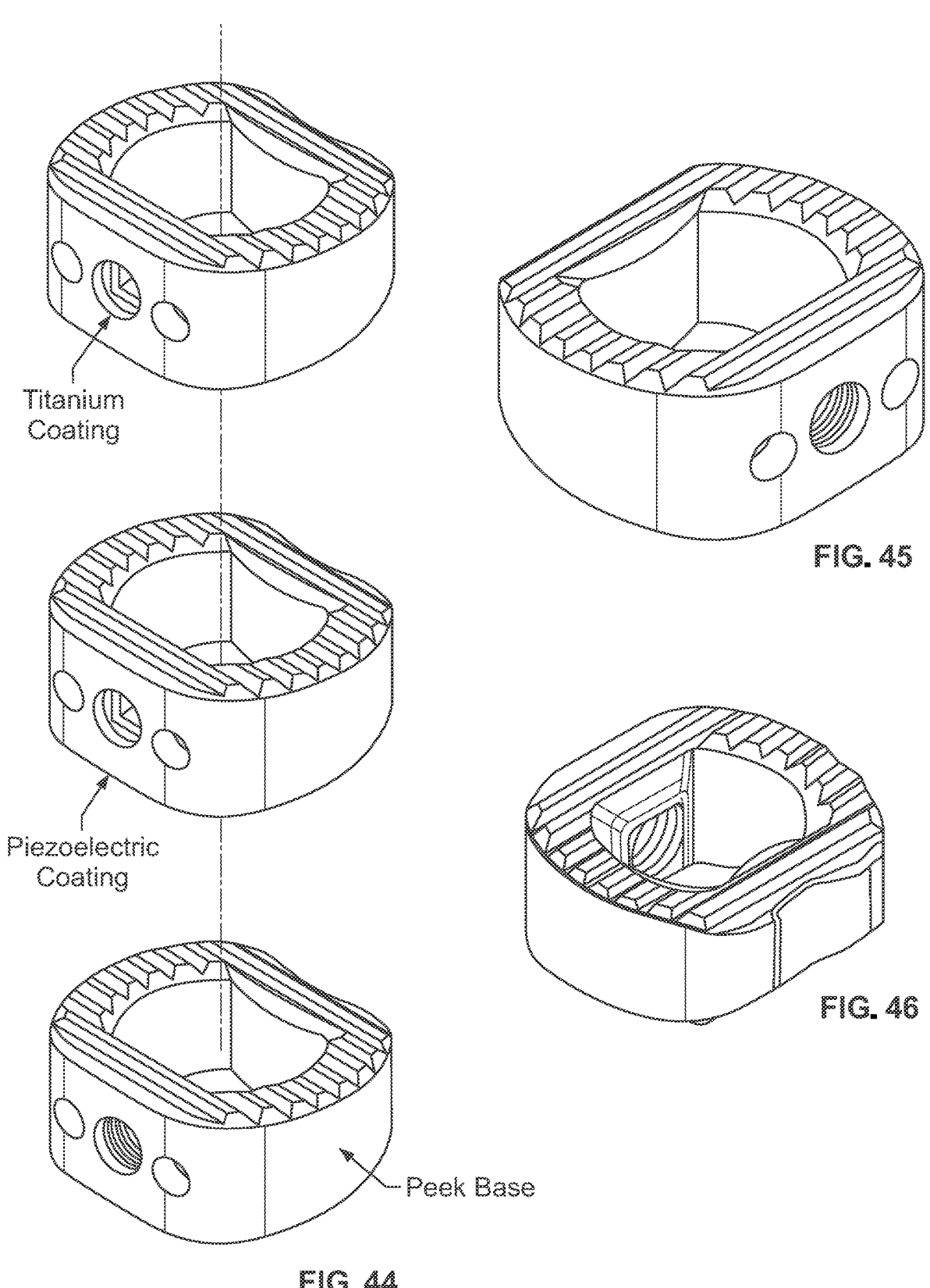

FIG. 44 is an exploded perspective view illustrating the electrically-conductive coating shown as a shell (e.g., a titanium or other electrically-conductive coating provided via sputtering, plasma spraying, sol-gel, physical vapor deposition, or other suitable process, etc.), the piezoelectric coating (e.g., piezoelectric poled PVDF dipped coating, etc.), and the base (e.g., PEEK base, etc.) of the piezoelectric implant shown in FIGS. 36-43. The electrically-conductive coating may be configured such that an entire outside of the piezoelectric implant has a negative charge.

FIGS. 45 and 46 are perspective views of a piezoelectric implant (e.g., for use as a spinal fusion implant, etc.) according to an exemplary embodiment.

Figure 47:
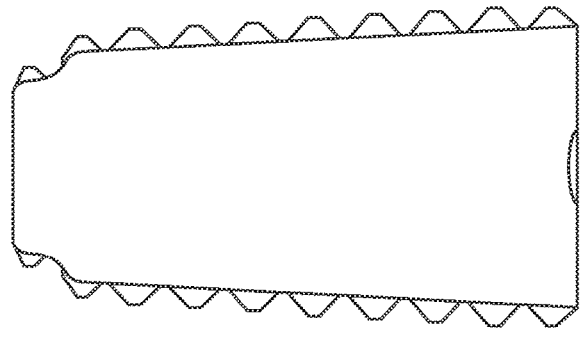

FIG. 47 is a side view of the piezoelectric implant shown in FIG. 45.

Figure 48:
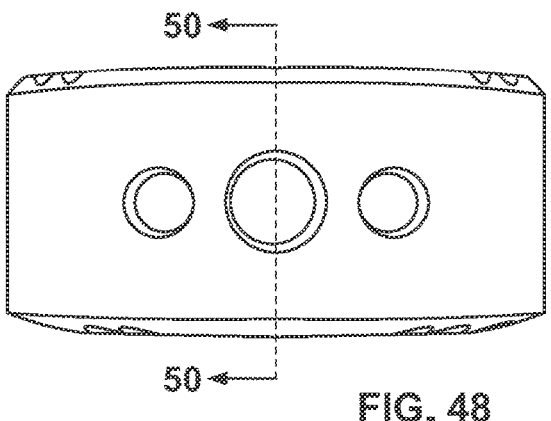

FIG. 48 is a front view of the piezoelectric implant shown in FIG. 45.

Figure 49:
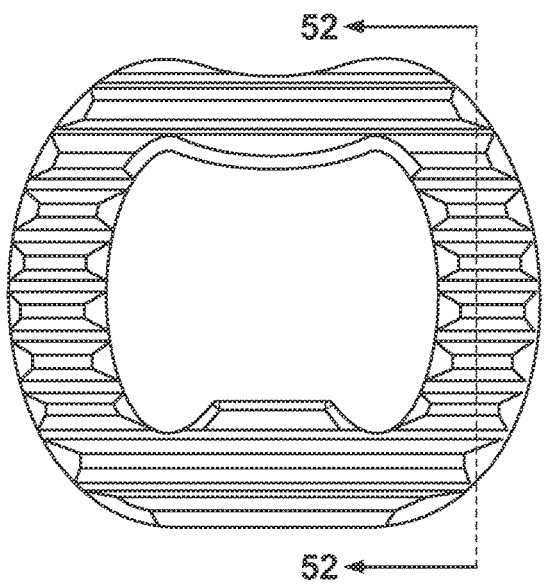

FIG. 49 is a top view of the piezoelectric implant shown in FIG. 45.

FIG. 50 is a cross-sectional view taken along the line 50-50 in FIG. 48.

FIG. 51 is a detailed view of the portion in FIG. 50 at a scale of 10:1.

FIG. 52 is a cross-sectional view taken along the line 52-52 in FIG. 49.

Figures 53, 54:
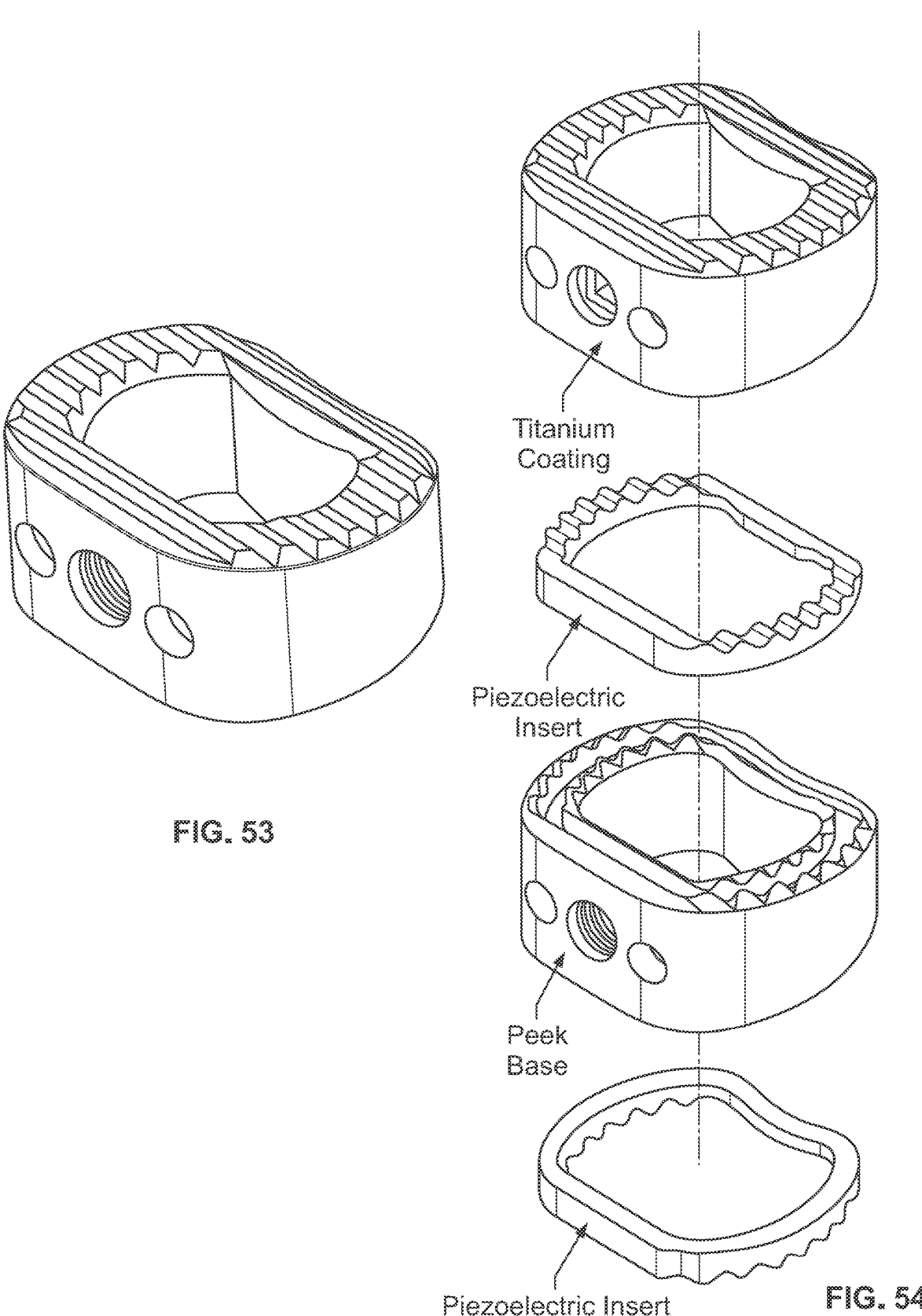

FIG. 53 is a perspective view of the piezoelectric implant shown in FIG. 45 before titanium sputtering.

FIG. 54 is an exploded perspective view illustrating the electrically-conductive coating shown as a shell (e.g., a titanium or other electrically-conductive coating provided via sputtering, plasma spraying, sol-gel, physical vapor deposition, or other suitable process, etc.), the piezoelectric inserts (e.g., piezoelectric poled PVDF inserts, etc.) and the base (e.g., PEEK base, etc.) of the piezoelectric implant shown in FIGS. 45-53. The electrically-conductive coating may be configured such that an entire outside of the piezo-electric implant has a negative charge. The piezoelectric inserts may be bonded to the base with electrically non-conductive or dielectric adhesive.

DETAILED DESCRIPTION

Example embodiments will now be described more fully with reference to the accompanying drawings.

Disclosed are exemplary embodiments of materials for piezoelectric implants. In exemplary embodiments, a material for a piezoelectric implant comprises a compounded material including barium titanate. In other exemplary embodiments, a material for a piezoelectric implant comprises a homogeneous material including ceramic material (s) doped with barium titanate. In additional exemplary embodiments, a material for a piezoelectric implant comprises polylactide (Poly(lactic acid), PLA) (e.g., PLLA, PDLA, PDLLA, etc.) poled to be piezoelectric. In further exemplary embodiments, a material for a piezoelectric implant comprises polyvinylidene fluoride (PVDF) poled to be piezoelectric. In other exemplary embodiments, a material for a piezoelectric implant comprises potassium sodium niobate (KNN) poled to be piezoelectric.

In yet other exemplary embodiments, the structural substrate or base (e.g., PEEK, etc.) of a piezoelectric implant may be dipped into a liquid material to thereby coat and encapsulate the structural substrate or base with the material, which material would thereafter be poled to be piezoelectric. The liquid material may comprise liquid polyvinylidene fluoride (PVDF), liquid polylactide (Poly(lactic acid), PLA) (e.g., PLLA, PDLA, PDLLA, etc.), liquid potassium sodium niobate (KNN, etc. The structural substrate or base of the piezoelectric implant may comprise polyetheretherketone (PEEK), polyetherketoneketone (PEKK), a thermoplastic polymer in the polyaryletherketone (PAEK) family, other thermoplastic polymer(s), other thermoplastic material(s), zirconium, zirconia, ZTA (zirconia toughen alumina), sili-con, and/or other ceramic material(s), etc.

Also disclosed are exemplary methods of poling materials (e.g., compounded materials including barium titanate, ceramic material(s) doped with barium titanate, PVDF, PLLA, KNN, etc.) for piezoelectric response for bone growth stimulation. Additional exemplary embodiments are disclosed of piezoelectric implants (e.g., a piezoelectric spinal fusion implant, a piezoelectric cranial implant, other orthopedic piezoelectric implant, veterinary/animal piezoelectric implant, etc.) comprising (e.g., injection molded from, etc.) one or more materials disclosed herein, such as a compounded material including barium titanate, a homogeneous material including ceramic material(s) doped with barium titanate, PVDF, PLA, KNN, other materials disclosed herein.

In exemplary embodiments, a compounded material comprises barium titanate and a thermoplastic material, such as polyetheretherketone (PEEK), polyetherketoneketone (PEKK), a thermoplastic polymer in the polyaryletherketone (PAEK) family, other thermoplastic polymer(s), other thermoplastic material(s), etc. The compounded material comprising barium titanate and thermoplastic material may be annealed in exemplary embodiments.

In other exemplary embodiments, a homogeneous material comprises one or more of zirconium, zirconia, ZTA (zirconia toughen alumina), silicon, other ceramic material(s) that has been doped with barium titanate. The homogeneous material comprising ceramic material doped with barium titanate may be sintered in exemplary embodiments.

In additional exemplary embodiments, a material for a piezoelectric implant comprises polylactide (Poly(lactic acid), PLA) (e.g., PLLA, PDLA, PDLLA, etc.) poled to be piezoelectric. For example, PLLA may be poled to be dielectric independent of or without needing barium titanate. The PLLA may be usable as a single homogeneous piezoelectric material for a piezoelectric implant, e.g., instead of or in addition to using a compounded material including barium titanate, etc. By way of further example, piezoelectric poled PLLA may be bonded to surfaces of a compounded material including barium titanate and thermoplastic and/or to surfaces of a homogeneous material including ceramic material doped with barium titanate.

In further exemplary embodiments, a material for a piezoelectric implant comprises polyvinylidene fluoride (PVDF) poled to be piezoelectric. PVDF may be poled to be dielectric independent of or without needing barium titanate. The poled PVDF may be used for a piezoelectric implant, e.g., instead of or in addition to using a compounded material including barium titanate, etc. For example, one or more poled piezoelectric PVDF films, sheets, or layers may bonded to (e.g., wrapped around and/or fused, etc.) to surfaces of a compounded material including barium titanate and thermoplastic and/or to surfaces of a homogeneous material including ceramic material doped with barium titanate.

In other exemplary embodiments, a material for a piezoelectric implant comprises potassium sodium niobate (KNN) poled to be piezoelectric. KNN may be poled to be dielectric independent of or without needing barium titanate. The poled KNN may be used for a piezoelectric implant, e.g., instead of or in addition to using a compounded material including barium titanate, etc. For example, one or more poled piezoelectric KNN films, sheets, or layers may bonded to (e.g., wrapped around and/or fused, etc.) to surfaces of a compounded material including barium titanate and thermoplastic and/or to surfaces of a homogeneous material including ceramic material doped with barium titanate.

Generally, compounding is a process of mixing or blending a base resin and one or more additives. Compounding is typically performed in the molten state to achieve a homo-geneous blend of the base resin and additives. In exemplary embodiments disclosed herein, PEEK (or other thermoplastic polymer) is compounded with barium titanate to provide a homogeneous compounded blend of the PEEK and barium titanate. By way of example, the barium titanate may be in the form of spheres and/or fibers, etc. The PEEK and barium titanate may be fed through an extruder (e.g., twin screw extruder, etc.) or other suitable compounder in which the PEEK and barium titanate are blended. The melted homogeneous blend of the PEEK and barium titanate may exit the extruder in strands. After the strands have cooled, the strands may be pelletized and formed into pellets suitable for injection molding of piezoelectric implants (e.g., an injection molded single-piece piezoelectric spinal fusion, cranial, orthopedic, or veterinary/animal implant having a monolithic construction, etc.). In this example, the PEEK was compounded with barium titanate. But in other exemplary embodiments, other materials may be compounded with barium titanate, such as polyetherketoneketone (PEKK), a thermoplastic polymer in the polyaryletherketone (PAEK) family, other thermoplastic polymer(s), other thermoplastic material(s). Accordingly, all exemplary embodiments disclosed herein do not necessarily require or are not limited to PEEK. In addition, all exemplary embodiments disclosed herein do not necessarily require or are not limited to barium titanate.

In exemplary embodiments, one or more films, sheets, or layers of material (e.g., polyvinylidene fluoride (PVDF), polylactide (Poly(lactic acid) PLA), potassium sodium niobate (KNN), etc.) that has been poled to be piezoelectric is bonded (e.g., wrapped around and/or fused, etc.) to surfaces of a compounded material including barium titanate and thermoplastic and/or to surfaces of a homogeneous material including ceramic material doped with barium titanate.

For example, a relatively thin film, sheet, or layer of PVDF may be poled to be piezoelectric. The PVDF film, sheet, or layer may be piezoelectric without needing barium titanate to be piezoelectric. The piezoelectric PVDF film, sheet, or layer may then be bonded to a compounded material that comprises barium titanate and thermoplastic material and/or to a homogeneous material that comprises ceramic material doped with barium titanate.

By way of further example, a relatively thin film, sheet, or layer of PLA (e.g., PLLA, PDLA, PDLLA, etc.) may be poled to be piezoelectric. The PLA film, sheet, or layer film may then be bonded to a compounded material that comprises barium titanate and thermoplastic material and/or to a homogeneous material that comprises ceramic material doped with barium titanate.

As a further example, a relatively thin film, sheet, or layer of KNN may be poled to be piezoelectric. The KNN film, sheet, or layer may then be bonded to a compounded material that comprises barium titanate and thermoplastic material and/or to a homogeneous material that comprises ceramic material doped with barium titanate.

In exemplary embodiments, a compounded material comprises the barium titanate and polyetheretherketone (PEEK). The compounded material may comprise a homogeneous compounded blend of the polyetheretherketone and the barium titanate.

In exemplary embodiments, the compounded material comprises the barium titanate and at least one other material. For example, the compounded material may comprise the barium titanate and at least one other material including one or more of polyetheretherketone (PEEK), polyetherketoneketone (PEKK), a thermoplastic polymer in the polyaryletherketone (PAEK) family, other thermoplastic polymer(s), other thermoplastic material(s), etc.

In an exemplary embodiment, a compounded material includes about 40 percent by weight of the barium titanate, and/or the compounded material includes about 12.62 percent by volume of the barium titanate.

In an exemplary embodiment, a compounded material includes about 50 percent by weight of the barium titanate, and/or the compounded material includes about 17.8 percent by volume of the barium titanate.

In an exemplary embodiment, a compounded material includes about 60 percent by weight of the barium titanate, and/or the compounded material includes about 24.52 percent by volume of the barium titanate.

In an exemplary embodiment, a compounded material includes about 70 percent by weight of the barium titanate, and/or the compounded material includes about 33.57 percent by volume of the barium titanate.

In an exemplary embodiment, a compounded material includes about 80 percent by weight of the barium titanate, and/or the compounded material includes about 46.42 percent by volume of the barium titanate.

In an exemplary embodiment, a compounded material includes about 30 percent by weight of polyetheretherketone; and/or the compounded material includes about 66.5 percent by volume of polyetheretherketone.

In exemplary embodiments, the compounded material includes a top surface and a bottom surface. The compounded material is poled or configured to have a negative charge along the top and bottom surfaces.

In exemplary embodiments, the compounded material includes a top surface, a bottom surface, and at least one tunnel. The at least one tunnel has an open end in one of a top or bottom surface and extending from the one of said top or bottom surface towards the other one of said top or bottom surface. The at least one tunnel does not extend completely through the other one of said top or bottom surface such that the at least one tunnel has a closed end adjacent the other one of said top or bottom surface. The compounded material is configured to have a negative charge along the top and bottom surfaces.

In exemplary embodiments, the compounded material includes first and second corners diagonally opposite each other and third and fourth diagonally opposite each other. The compounded material also includes first, second, third, and fourth tunnels respectively adjacent the first, second, third, and fourth corners of the compounded material. Each of the first and second tunnels starts at an opening defined in the top surface and extends downwardly from the top surface towards the bottom surface. The first and second tunnels do not extend completely through the bottom surface such that each of the first and second tunnels has a closed end adjacent the bottom surface. Each of the third and fourth tunnels starts at an opening defined in the bottom surface and extends upwardly from the bottom surface towards the top surface. The third and fourth tunnels do not extend completely through the top surface such that each of the third and fourth tunnels has a closed end adjacent the top surface.

In exemplary embodiments, the compounded material is poled at a temperature less than the Curie temperature of the barium titanate, and the poled compounded material is piezoelectric.

In exemplary embodiments, the compounded material is poled at room temperature within a range from about 20° C. to 22° C., and the poled compounded material is piezoelectric.

In exemplary embodiments, the compounded material has a piezoelectric modulus or piezoelectric coefficient (D33) within a range from 4 to 33 (e.g., from 5 to 23, etc.). The D33 range from 4 to 33 is an example as other exemplary embodiments may be configured differently, such that the compounded material has a piezoelectric modulus or piezoelectric coefficient (D33) less than 4 or greater than 33.

In exemplary embodiments, the compounded material consists only of polyetheretherketone and the barium titanate.

In exemplary embodiments, a piezoelectric implant comprises a compounded material as disclosed herein. The piezoelectric implant may be injection molded from the compounded material such that the piezoelectric implant has a monolithic, single-piece construction. The piezoelectric implant may comprise a spinal fusion piezoelectric implant, cranial piezoelectric implant, orthopedic piezoelectric implant, a veterinary/animal piezoelectric implant, etc.

In exemplary embodiments, a method comprises prepoling a material that includes barium titanate by annealing the material during which pressure and electrical current is applied to the compounded material; or extruding the material during which electrical current is applied to the compounded material.

In exemplary embodiments, a method includes compounding polyetheretherketone with the barium titanate to thereby provide a homogeneous compounded blend of the polyetheretherketone and the barium titanate; and thereafter poling the homogeneous compounded blend of the polyetheretherketone and the barium titanate for piezoelectric response.

In exemplary embodiments, a method comprises poling a material including barium titanate and thermoplastic polymer for piezoelectric response at a temperature less than the Curie temperature of the barium titanate and less than the glass transition temperature of the thermoplastic polymer.

In exemplary embodiments, the thermoplastic polymer comprises polyetheretherketone, polyetherketoneketone, another thermoplastic polymer in the polyaryletherketone family, other thermoplastic polymer(s).

In exemplary embodiments, the method includes poling the material at room temperature within a range from about 20° C. to 22° C.

In exemplary embodiments, the poling includes applying an electric charge of about 75 kilovolts to the material for about 5 minutes at room temperature in a silicone oil bath without first heating the material.

In exemplary embodiments, the method includes compounding polyetheretherketone with the barium titanate to thereby provide a homogeneous compounded blend of the polyetheretherketone and the barium titanate; and thereafter poling the homogeneous compounded blend of the polyetheretherketone and the barium titanate for piezoelectric response at the temperature less than the Curie temperature of the barium titanate and less than the glass transition temperature of the polyetheretherketone. The homogeneous compounded blend of the polyetheretherketone and the barium titanate may consist only of the polyetheretherketone and the barium titanate. The method may further include injection molding the homogeneous compounded blend of the polyetheretherketone and the barium titanate into a single-piece piezoelectric implant having a monolithic construction.

In exemplary embodiments, the material includes about 33.5 percent by volume of the barium titanate; and/or the material includes about 70 percent by weight of the barium titanate. The material may include about 66.5 percent by volume of polyetheretherketone; and/or the material may include about 30 percent by weight of polyetheretherketone.

In an exemplary embodiment, a compounded material includes about 40 percent by weight of the barium titanate, and/or the compounded material includes about 12.62 percent by volume of the barium titanate. In an exemplary embodiment, a compounded material includes about 50 percent by weight of the barium titanate, and/or the compounded material includes about 17.8 percent by volume of the barium titanate. In an exemplary embodiment, a compounded material includes about 60 percent by weight of the barium titanate, and/or the compounded material includes about 24.52 percent by volume of the barium titanate. In an exemplary embodiment, a compounded material includes about 80 percent by weight of the barium titanate, and/or the compounded material includes about 46.42 percent by volume of the barium titanate.

In exemplary embodiments, the method includes poling the material to have a negative charge along top and bottom surfaces of the material.

In exemplary embodiments, the method includes forming at least one tunnel in the material having an open end in one of a top or bottom surface of the compounded material and that extends from the one of said top or bottom surface towards the other one of said top or bottom surface. The at least one tunnel does not extend completely through the other one of said top or bottom surface such that the at least one tunnel has a closed end adjacent the other one of said top or bottom surface.

In exemplary embodiments, the material includes first and second corners diagonally opposite each other and third and fourth diagonally opposite each other. The method includes forming first, second, third, and fourth tunnels respectively adjacent the first, second, third, and fourth corners of the compounded material. Each of the first and second tunnels starts at an opening defined in the top surface and extends downwardly from the top surface towards the bottom surface. The first and second tunnels do not extend completely through the bottom surface such that each of the first and second tunnels has a closed end adjacent the bottom surface. Each of the third and fourth tunnels starts at an opening defined in the bottom surface and extends upwardly from the bottom surface towards the top surface. The third and fourth tunnels do not extend completely through the top surface such that each of the third and fourth tunnels has a closed end adjacent the top surface.

In exemplary embodiments, the material including the barium titanate and thermoplastic polymer has a piezoelectric modulus or piezoelectric coefficient (D33) within a range from 4 to 33 (e.g., from 5 to 23, etc.). The D33 range from 4 to 33 is an example as other exemplary embodiments may be configured differently, such that the material including the barium titanate and thermoplastic polymer a piezoelectric modulus or piezoelectric coefficient (D33) less than 4 or greater than 33.

In exemplary embodiments, the material further includes one or more functional fillers. For example, the material may include hydroxyapatite (HA). Or, for example, the material may include one or more functional fillers that may be added to the compounder for extending the life of a compounded material for bioresorbable (e.g., PLLA) implants to a predetermined time period for the piezoelectric implant to be made from the compounded material.

In exemplary embodiments, a piezoelectric implant comprises a material including barium titanate compounded with thermoplastic polymer and/or ceramic material doped with barium titanate. The piezoelectric implant may be injection molded from the material such that the piezoelectric implant has a monolithic, single-piece construction. The piezoelectric implant may comprise a spinal fusion piezoelectric implant, a cranial. In other exemplary embodiments, the piezoelectric implant may comprise a cranial piezoelectric implant, other orthopedic piezoelectric implant, a piezoelectric implant for veterinary/animal purposes. Accordingly, aspects of the present disclosure should not be limited to any particular type of piezoelectric implant or be limited to use with only humans or animals.

Figure 1:
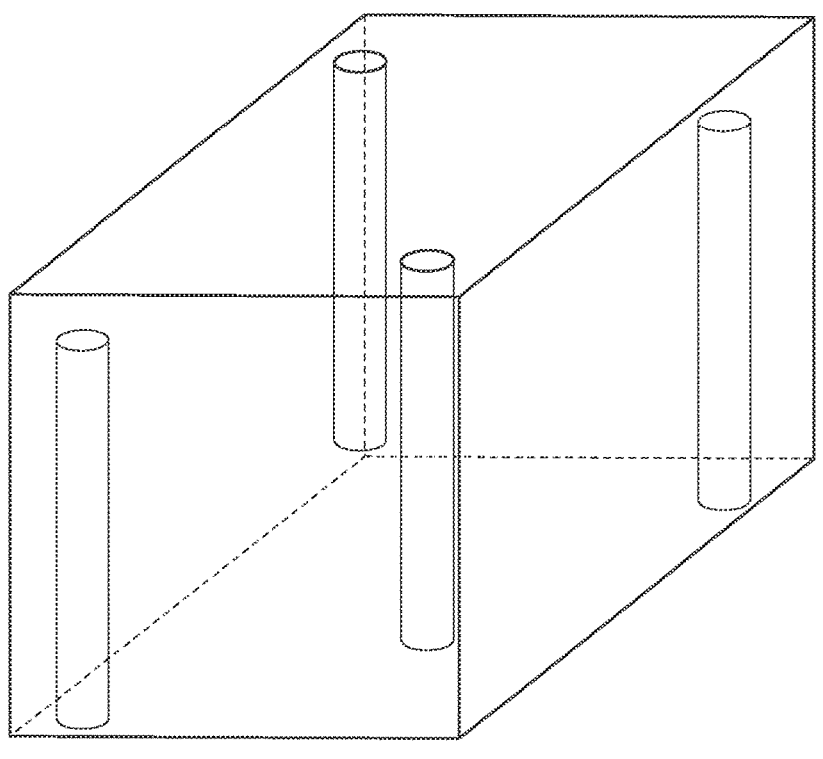
Figures 2, 3:
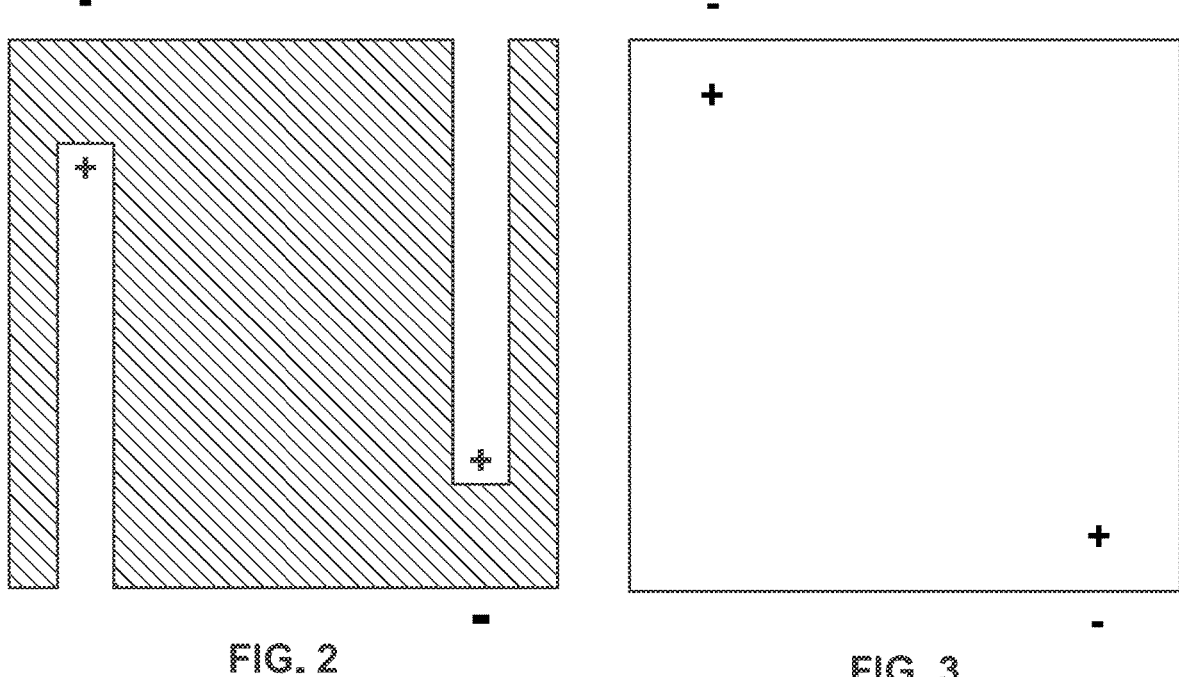
FIG. 2 is a cross-sectional view of the $BaTiO_3$/PEEK material shown in FIG. 1 taken along the tunnels and illustrating the negative charge along the top and bottom surfaces of the $BaTiO_3$/PEEK material.
FIG. 3 is a front end view of the $BaTiO_3$/PEEK material shown in FIG. 1 and illustrating the negative charge along the top and bottom surfaces of the $BaTiO_3$/PEEK material.
Figure 4:
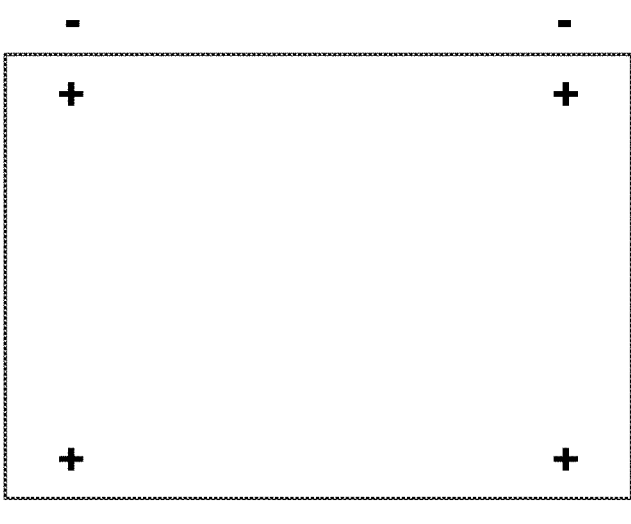
FIG. 4 is a side view of the $BaTiO_3$/PEEK material shown in FIG. 1 and illustrating the negative charge along the top and bottom surfaces of the $BaTiO_3$/PEEK material.

FIGS. 1-4 illustrate a material including barium titanate (BaTiO$_3$) and polyetheretherketone (PEEK) according to an exemplary embodiment in which tunnels or closed-ended holes have been formed (e.g., drilled, etc.) in the BaTiO$_3$/PEEK material. As shown, each of the four tunnels is adjacent a corresponding one of the four corners of the BaTiO$_3$/PEEK material. As shown in FIGS. 2-4, a negative charge is along the top and bottom surfaces of the BaTiO$_3$/PEEK material, thereby providing a negative charge for contacting surfaces of a piezoelectric implant. Although the example illustrated in FIGS. 1-4 includes PEEK, the material with the tunnels may include one or more other materials with barium titanate, such as polyetherketoneketone (PEKK), a thermoplastic polymer in the polyaryletherketone (PAEK) family, polylactide (Poly(lactic acid), PLA) (e.g., PLLA, PDLA, PDLLA, etc.), other thermoplastic polymer(s), other thermoplastic material(s), etc.

With continued reference to FIGS. 1-4, first and second tunnels are formed in the top surface of the BaTiO$_3$/PEEK at diagonally opposite first and second corners, respectively. Each of the first and second tunnels starts at an opening defined in the top surface and extends downwardly from the top surface towards the bottom surface of the BaTiO$_3$/PEEK material. The first and second tunnels are closed ended and do not extend completely through the bottom surface of the BaTiO$_3$/PEEK material.

Third and fourth tunnels are formed in the bottom surface of the BaTiO$_3$/PEEK at diagonally opposite third and fourth corners, respectively. Each of the third and fourth tunnels starts at an opening defined in the bottom surface and extends upwardly from the bottom surface towards the top surface of the BaTiO$_3$/PEEK material. The third and fourth tunnels are closed ended and do not extend completely through the top surface of the BaTiO$_3$/PEEK material. The tunnels may be operable for voltage spreading.

In exemplary embodiments, a metal with elasticity (e.g., porous titanium, etc.) may be used to create an electrode along the top and/or bottom surfaces and help disperse voltage from the tunnels. In exemplary embodiments, titanium or other suitable electrode coating may be sprayed, sputtered, applied via a sol-gel process, applied via a physical vapor deposition process, or otherwise coated or provided along at least portions of the top and bottom surfaces of an implant, which may promote better bone growth and voltage spreading. In some exemplary embodiments, titanium or other suitable coating encapsulates the entirety of the piezoelectric implant such that the entire outside of the piezoelectric implant has a negative charge (e.g., FIG. 15, FIG. 17, etc.).

In exemplary embodiments, the compounded material includes about 20 volume percent to about 30 volume percent of the barium titanate. In such exemplary embodiments, the compounded material may also include about 70 volume percent to about 80 volume percent of the PEEK.

In exemplary embodiments, the compounded material includes about 30 weight percent to about 80 weight percent of the barium titanate. In such exemplary embodiments, the compounded material may also include about 20 weight percent to about 70 weight percent of the PEEK.

In an exemplary embodiment, the compounded material may include about 8 volume percent of the barium titanate and about 92 volume percent of the polyetheretherketone. In such exemplary embodiment, the compounded material includes about 30 weight percent of the barium titanate and about 70 weight percent of the polyetheretherketone.

In an exemplary embodiment, the compounded material includes about 40 weight percent of the barium titanate and about 60 weight percent of the polyetheretherketone. In another exemplary embodiment, the compounded material includes about 50 weight percent of the barium titanate and about 50 weight percent of the polyetheretherketone. In a further exemplary embodiment, the compounded material includes about 60 weight percent of the barium titanate and about 40 weight percent of the polyetheretherketone. In an additional exemplary embodiment, the compounded material includes about 70 weight percent of the barium titanate and about 30 weight percent of the polyetheretherketone. In yet another exemplary embodiment, the compounded material includes about 80 weight percent of the barium titanate and about 20 weight percent of the polyetheretherketone.

By way of example, the barium titanate may comprise a barium titanate powder that does not include lead or cadmium and is biocompatible. The barium titanate may have a Curie temperature of about 120° C.

By way of further example, the PEEK may comprise polyetheretherketone supplied in pellet form. The PEEK may be highly dielectric with a dielectric strength of about 15 kilovolts per millimeter (kV/mm), a dielectric constant of about 0.001 at a frequency of 60 hertz (Hz), a dielectric constant of about 0.001 at a frequency of 1 kilohertz (kHz), and a dielectric constant of about 0.003 at a frequency of 1 megahertz (MHz). The PEEK may have a glass transition temperature of about 147° C.

Embodiments disclosed herein also include poling the compounded PEEK and barium titanate material for piezoelectric response for bone growth stimulation. Conventional poling methods typically include heating a specimen in a silicone oil bath and applying an electric charge to activate the specimen to produce a piezoelectric response. Contrary to the conventional methods, however, exemplary embodiments disclosed herein include poling the compounded PEEK and barium titanate material at room temperature (e.g., about 20° C., from about 20° C. to about 22° C., etc.) without first heating the compounded PEEK and barium titanate material in a silicone oil bath. Given that PEEK is highly dielectric with a glass transition temperature that is considerably higher than the Curie temperature of barium titanate, poling the compounded PEEK and barium titanate material at room temperature well below the Curie temperature of barium titanate is counterintuitive and contrary to conventional wisdom.

In exemplary methods, poling the compounded PEEK and barium titanate material may include applying an electric charge of about 75 kilovolts/75000 watts to the compounded material for about 5 minutes in a silicone oil bath at room temperature without heating. The poled compounded PEEK and barium titanate material produced a piezoelectric response within a range from about 1.5 picocoulombs per newton (pC/N) to about 2.5 pC/N. In other exemplary embodiments, the poling may produce a different piezoelectric response from the compounded PEEK and barium titanate material, e.g., from about 1.8 pC/N to about 3 pC/N, less than 30 pC/N, etc.

In exemplary embodiments, compounded PEEK and barium titanate material (or other materials disclosed herein) may be used to make piezoelectric implants. For example, a single-piece piezoelectric implant having a monolithic construction may be injection molded from compounded PEEK and barium titanate material or from another material disclosed herein. The single-piece piezoelectric implant may provide one or more (but not necessarily any or all) of the following advantages as compared to multi-piece piezoelectric implant assemblies. For example, a single-piece piezoelectric implant may be less prone to failure than multi-piece piezoelectric implant assemblies. A single-piece piezoelectric implant may require less time for sterilization as compared to having to sterilize multiple pieces of a multi-piece piezoelectric implant assembly. A single-piece piezoelectric implant made of a homogeneous blend of materials (e.g., a homogeneous blend of PEEK and barium titanate, etc.) may also avoid problems associated with different mismatched material properties (e.g., strength, elasticity, biocompatibility, etc.) of the different materials used for the different pieces in multi-piece piezoelectric implant assemblies. The single-piece piezoelectric implant may include only a single relatively large piece, thereby avoiding the use of the very small pieces and the time required to assemble the various small pieces into the multi-piece piezoelectric implant assembly.

In exemplary embodiments, one or more films, sheets, or layers of material (e.g., polyvinylidene fluoride (PVDF), potassium sodium niobate (KNN), polylactide (Poly(lactic acid) PLA) etc.) that have been poled to be piezoelectric are bonded to the surface of a compounded and/or homogeneous material as disclosed herein. For example, a relatively thin film, sheet, or layer of PVDF is poled to be piezoelectric. The PVDF film, sheet, or layer may be piezoelectric without needing barium titanate to be piezoelectric. The piezoelectric PVDF film, sheet, or layer is bonded to a compounded material that comprises barium titanate and at least one other material, including one or more of polyetheretherketone (PEEK), polyetherketoneketone (PEKK), a thermoplastic polymer in the polyaryletherketone (PAEK) family, other thermoplastic polymer(s), other thermoplastic material(s), etc. Or, for example, the piezoelectric PVDF film, sheet, or layer is bonded to a homogeneous material that comprises ceramic material (e.g., zirconium, zirconia, ZTA (zirconia toughen alumina), silicon, other ceramic material(s), etc.) doped with barium titanate.

In other exemplary embodiments, one or more relatively thins films, sheets, or layers of PLA (e.g., PLLA, PDLA, PDLLA, etc.) are poled to be piezoelectric. For example, a relatively thin film, sheet, or layer of PLLA is poled to be piezoelectric. The PLLA film, sheet, or layer may be piezoelectric without needing barium titanate to be piezoelectric. The piezoelectric PLLA is bonded to a compounded material that comprises barium titanate and at least one other material, including one or more of polyetheretherketone (PEEK), polyetherketoneketone (PEKK), a thermoplastic polymer in the polyaryletherketone (PAEK) family, other thermoplastic polymer(s), other thermoplastic material(s), etc. Or, for example, the piezoelectric PLLA film, sheet, or layer is bonded to a homogeneous material that comprises ceramic material (e.g., zirconium, zirconia, ZTA (zirconia toughen alumina), silicon, other ceramic material(s), etc.) doped with barium titanate.

In further exemplary embodiments, a relatively thin film, sheet, or layer of KNN is poled to be piezoelectric. The KNN film, sheet, or layer may be piezoelectric without needing barium titanate to be piezoelectric. The piezoelectric KNN film, sheet, or layer is bonded to a compounded material that comprises barium titanate and at least one other material, including one or more of polyetheretherketone (PEEK), polyetherketoneketone (PEKK), a thermoplastic polymer in the polyaryletherketone (PAEK) family, other thermoplastic polymer(s), other thermoplastic material(s), etc. Or, for example, the piezoelectric KNN film, sheet, or layer is bonded to a homogeneous material that comprises ceramic material (e.g., zirconium, zirconia, ZTA (zirconia toughen alumina), silicon, other ceramic material(s), etc.) doped with barium titanate.

In exemplary embodiments, titanium or other suitable electrode coating may be plasma sprayed, sputtered, applied via a sol-gel process, applied via a physical vapor deposition process, or otherwise coated or provided along one or more portions or along an entire outer surface a piezoelectric implant. The titanium or other electrode coating may be operable for spreading the charge/voltage that results as a piezoelectric response to strain. The titanium coating or other electrode coating will amplify the electric charge and carry the charge over a greater surface area than just where the piezoelectric elements are located. In these exemplary embodiments, the piezoelectric implant may be made from a compounded material including barium titanate, a homogeneous material including ceramic material doped with barium titanate, or other material.

In exemplary embodiments, a piezoelectric implant may include a titanium coating or other electrode coating along only predetermined portions of the piezoelectric implant that are configured to make physical contact with bone and/or that are configured to be compressed generally between the piezoelectric implant and bone. For example, the titanium coating or other electrode coating may be provided along outwardly protruding portions or ridges along the piezoelectric implant's top and bottom surfaces.

In other exemplary embodiments, a piezoelectric implant may include a titanium coating or other electrode coating (broadly, an electrically-conductive coating) that defines and/or is disposed over the entire outside of the piezoelectric implant. The titanium coating or other electrode coating (e.g., a titanium shell encapsulation, etc.) may fully encapsulate the entire piezoelectric implant. The titanium or other electrically-conductive coating may be configured such that the entire outside of the piezoelectric implant has a negative charge (e.g., FIG. 15, FIG. 17, etc.). The amplified negative side is much more negative than the inverse positive side. This inhibits or prevents short circuiting because the positive charge is very small relative to the negative charge, and the negatively charged side has a sufficiently high enough negative charge to overtake the positively charged side.

FIG. 15 shows a negative charge around the entire outer surface of the piezoelectric implant even though the electrode grounded out the positive charge. With reference to FIG. 16, A references an electrode coating (e.g., titanium, other electrically-conductive coating, etc.) around entire outside, B references piezoelectric elements having their negative sides facing outwardly/away, C references an electrically non-conductive or dielectric adhesive without any electrode coating, and D references a base or substrate structure of the piezoelectric implant.

FIG. 17 also shows a negative charge around the entire outer surface of the piezoelectric implant according to another exemplary embodiment. In FIG. 17, E references a thermal polymer (e.g., PEEK, other materials disclosed herein, etc.), F references an electrically non-conductive or dielectric adhesive (e.g., light cured biocompatible epoxy, etc.), G references piezoelectric elements, and H references an electrically-conductive coating (e.g., a titanium or other electrically-conductive coating provided via sputtering, plasma spraying, sol-gel, physical vapor deposition, or other suitable process, etc.).

A references an electrode coating (e.g., titanium, other electrically-conductive coating, etc.) around entire outside, B references piezoelectric elements having their negative sides facing outwardly/away, C references an electrically non-conductive or dielectric adhesive without any electrode coating, and D references a base or substrate structure of the piezoelectric implant.

FIGS. 5-14 illustrate a piezoelectric implant (e.g., for use as a spinal fusion implant, etc.) according to an exemplary embodiment. In this exemplary embodiment, the piezoelectric implant includes a base (e.g., PEEK or other suitable material, etc.), piezoelectric elements (e.g., pre-poled piezoelectric PVDF films laminated, etc.) along at least the outermost protruding portions of one more ridges defined by the base, and an electrode coating or shell encapsulation (e.g., a titanium or other electrically-conductive coating provided via sputtering, plasma spraying, sol-gel, physical vapor deposition process, or other suitable process, etc.).

In this exemplary embodiment, the base comprises polyetheretherketone (PEEK). But other suitable materials may also be used for the base, such as polyetherketoneketone (PEKK), a thermoplastic polymer in the polyaryletherketone (PAEK) family, other thermoplastic polymer(s), other thermoplastic material(s), zirconium, zirconia, ZTA (zirconia toughen alumina), silicon, other ceramic material(s), etc.

As shown in FIGS. 10-13, the piezoelectric elements are disposed along at least the outermost protruding portions of ridges defined by the base. Accordingly, the piezoelectric elements are thus disposed along portions of the piezoelectric implant that are configured to make physical contact with bone and/or that are configured to be compressed generally between the piezoelectric implant and bone.

In this exemplary embodiment, the piezoelectric elements comprise polyvinylidene fluoride (PVDF) films poled to be piezoelectric. The PVDF films are laminated or otherwise bonded to the PEEK base such that the PVDF films' negative sides face outward and positive sides face inward. The PVDF films are along the outermost protruding portions of the ridges where compression occurs. In this exemplary embodiment, the PVDF films are not disposed in the valleys, troughs, or channels or along sidewalls of the piezoelectric implant. In other exemplary embodiments, the PVDF films or other piezoelectric elements may be disposed within the valleys, troughs, or channels. One or more other materials (e.g., electrically non-conductive or dielectric adhesive, etc.) may also be provided in the valleys, troughs, or channels to strengthen and/or to reinforce he piezoelectric implant for distribution of forces. As a further example, the PVDF films or other piezoelectric elements may be disposed over the entire top and bottom sides of the piezoelectric implant, e.g., within the valleys, troughs, or channels and along the entirety of the ridges. In this latter example, an electrically non-conductive or dielectric adhesive or other suitable material(s) may be disposed over the PVDF films and/or may fill up the valleys, troughs, or channels to address and/or inhibit delamination of the PVDF films from the PEEK base.

This exemplary embodiment includes piezo lamination in the form of PVDF films laminated to the base. Alternative processes besides lamination may be used for providing or bonding the piezoelectric elements to the base and/or other materials besides PVDF films may be used for the piezoelectric elements. For example, the piezoelectric elements may comprise potassium sodium niobate (KNN) poled to be piezoelectric. Or, for example, the piezoelectric elements may comprise polylactide (Poly(lactic acid), PLA) (e.g., PLLA, PDLA, PDLLA, etc.) poled to be piezoelectric.

Figure 5:
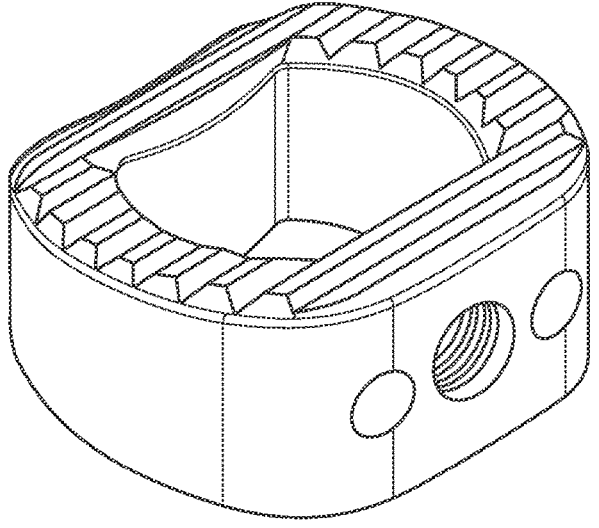
FIGS. 5 and 6 are perspective views of a piezoelectric implant (e.g., for use as a spinal fusion implant, etc.) according to an exemplary embodiment.
Figure 6:
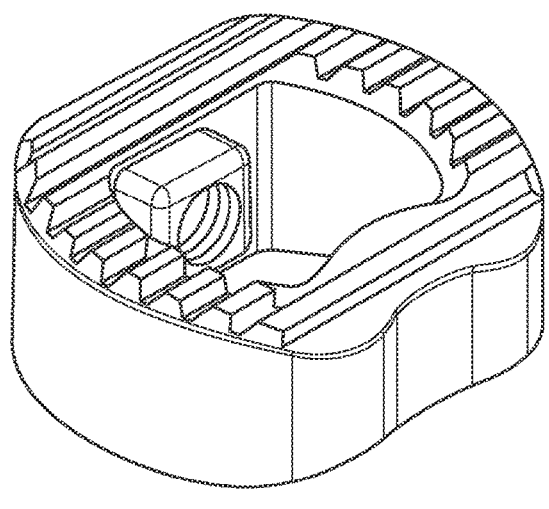
Figure 7:
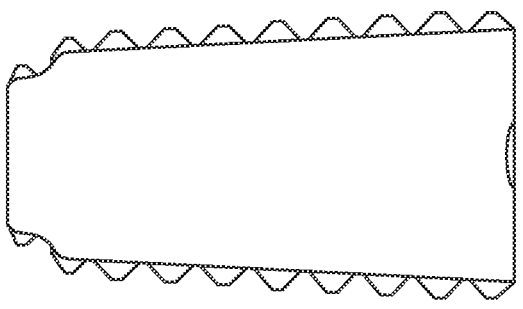
FIG. 7 is a side view of the piezoelectric implant shown in FIG. 5.
Figure 8:
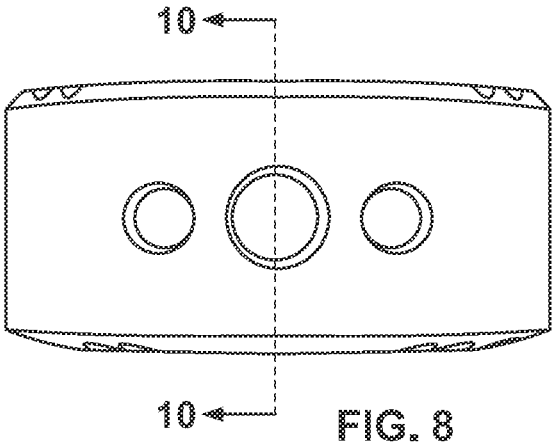
FIG. 8 is a front view of the piezoelectric implant shown in FIG. 5.
Figure 9:
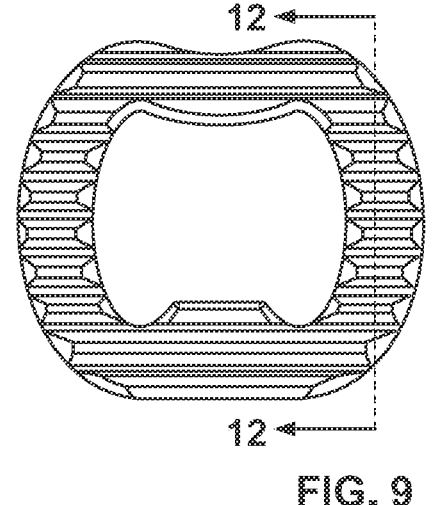
FIG. 9 is a top view of the piezoelectric implant shown in FIG. 5.
Figures 10, 11, 12:
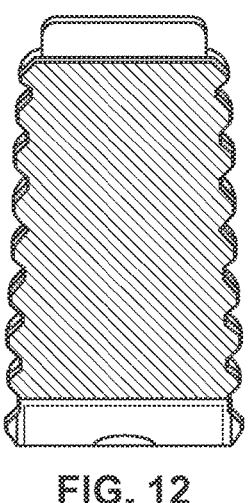
FIG. 10 is a cross-sectional view taken along the line 10-10 in FIG. 8.
FIG. 11 is a detailed view of the portion in FIG. 10 at a scale of 10:1.
FIG. 12 is a cross-sectional view taken along the line 12-12 in FIG. 9.
Figure 13:
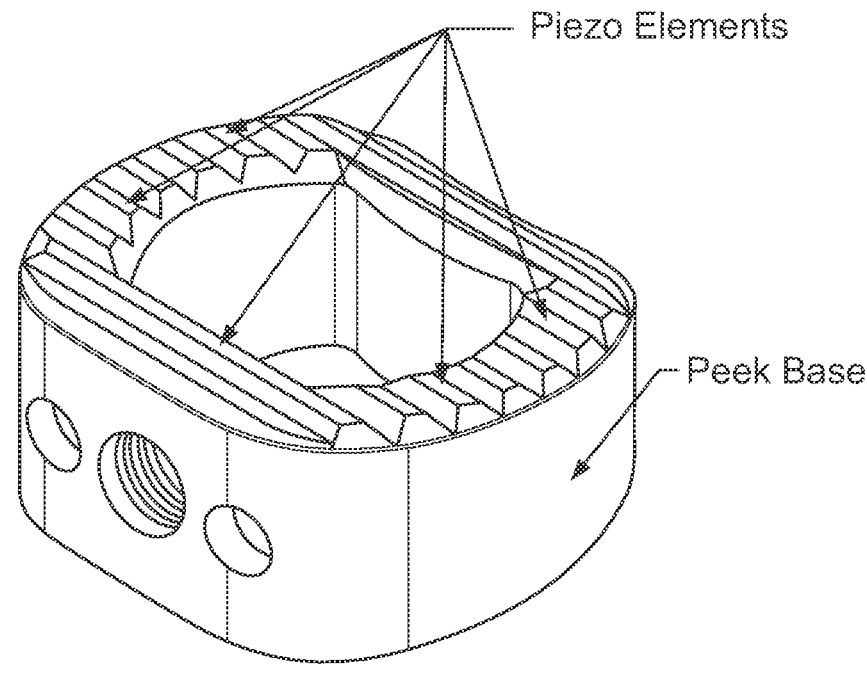
FIG. 13 is a perspective view of the piezoelectric implant shown in FIG. 5 without an electrode or electrically-conductive coating to illustrate the location of piezoelectric elements (e.g., pre-poled piezoelectric PVDF films laminated, etc.) along at least the outermost protruding portions of ridges defined by a base (e.g., PEEK or other suitable material, etc.).
Figure 14:
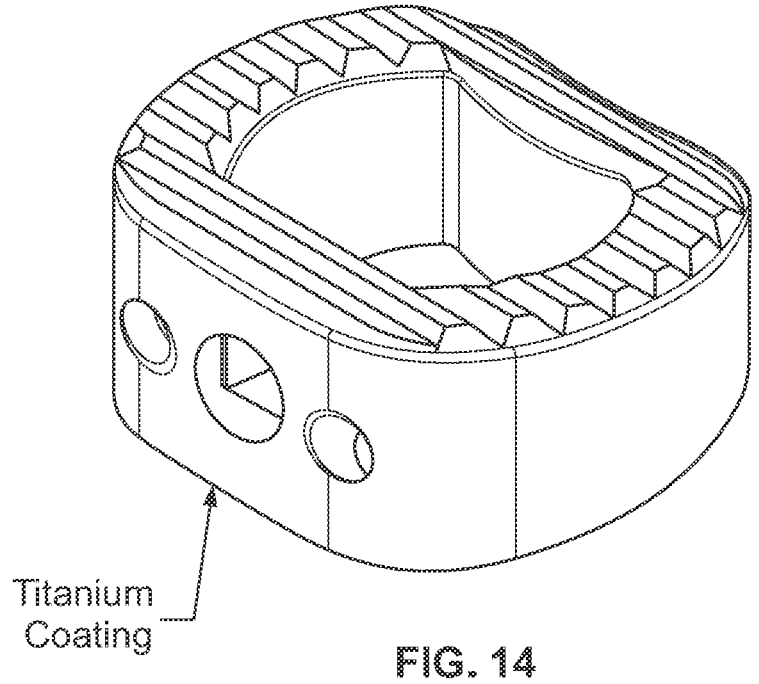
FIG. 14 is a perspective view illustrating an electrically-conductive coating shown as a shell (e.g., a titanium or other electrically-conductive coating provided via sputtering, plasma spraying, sol-gel, physical vapor deposition, or other suitable process, etc.) for the piezoelectric implant shown in FIG. 13 such that an entire outside of the piezoelectric implant has a negative charge.

FIG. 13 illustrates the piezoelectric implant shown in FIG. 5 without an electrode coating to illustrate the location of piezoelectric elements (e.g., pre-poled piezoelectric PVDF films laminated, etc.) along at least the outermost protruding portions of ridges defined by the base (e.g., PEEK or other suitable material, etc.). FIG. 14 illustrates an electrically-conductive coating shown as a shell (e.g., a titanium or other electrically-conductive coating provided via sputtering, plasma spraying, sol-gel, physical vapor deposition, or other suitable process, etc.) for the piezoelectric implant shown in FIG. 13 such that an entire outside of the piezoelectric implant has a negative charge as discussed above and shown in FIG. 15.

FIGS. 18-26 illustrate a piezoelectric implant (e.g., for use as a spinal fusion implant, etc.) according to an exemplary embodiment. In this exemplary embodiment, the piezoelectric implant includes a base (e.g., PEEK or other suitable material, etc.), piezoelectric elements (e.g., pre-poled piezoelectric PVDF inserts, etc.), and an electrically-conductive coating or shell encapsulation (e.g., a titanium or other electrically-conductive coating provided via sputtering, plasma spraying, sol-gel, physical vapor deposition process, or other suitable process, etc.). The electrically-conductive coating may be configured such that an entire outside of the piezoelectric implant has a negative charge.

In this exemplary embodiment, the base comprises polyetheretherketone (PEEK). But other suitable materials may also be used for the base, such as polyetherketoneketone (PEKK), a thermoplastic polymer in the polyaryletherketone (PAEK) family, other thermoplastic polymer(s), other thermoplastic material(s), zirconium, zirconia, ZTA (zirconia toughen alumina), silicon, other ceramic material(s), etc.

In this exemplary embodiment, the piezoelectric elements comprise polyvinylidene fluoride (PVDF) inserts poled to be piezoelectric. The PEEK base is between the piezoelectric inserts as shown in FIG. 25, such that the piezoelectric inserts' negative sides face outward and positive sides face inward. The piezoelectric inserts define protruding portions or ridges where compression occurs. Other materials besides PVDF may be used for the piezoelectric elements. For example, the piezoelectric elements may comprise potassium sodium niobate (KNN) poled to be piezoelectric. Or, for example, the piezoelectric elements may comprise polylactide (Poly(lactic acid), PLA) (e.g., PLLA, PDLA, PDLLA, etc.) poled to be piezoelectric.

FIGS. 27-35 illustrate a piezoelectric implant (e.g., for use as a spinal fusion implant, etc.) according to an exemplary embodiment. In this exemplary embodiment, the piezoelectric implant includes a piezoelectric base (e.g., a piezoelectric poled PVDF base, other suitable material, etc.) and an electrically-conductive coating or shell encapsulation (e.g., a titanium or other electrically-conductive coating provided via sputtering, plasma spraying, sol-gel, physical vapor deposition process, or other suitable process, etc.). The electrically-conductive coating may be configured such that an entire outside of the piezoelectric implant has a negative charge.

In this exemplary embodiment, the piezoelectric base comprises piezoelectric poled PVDF base. But other materials besides PVDF may be used for the piezoelectric base. For example, the piezoelectric base may comprise potassium sodium niobate (KNN) poled to be piezoelectric. Or, for example, the piezoelectric base may comprise polylactide (Poly(lactic acid), PLA) (e.g., PLLA, PDLA, PDLLA, etc.) poled to be piezoelectric.

FIGS. 36-44 illustrate a piezoelectric implant (e.g., for use as a spinal fusion implant, etc.) according to an exemplary embodiment. In this exemplary embodiment, the piezoelectric implant includes a base (e.g., PEEK or other suitable material, etc.), a piezoelectric coating (e.g., piezoelectric poled PVDF dipped coating, etc.), and an electrically-conducting or shell encapsulation (e.g., a titanium or other electrically-conductive coating provided via sputtering, plasma spraying, sol-gel, physical vapor deposition process, or other suitable process, etc.). The electrically-conductive coating may be configured such that an entire outside of the piezoelectric implant has a negative charge.

In this exemplary embodiment, the base comprises polyetheretherketone (PEEK). But other suitable materials may also be used for the base, such as polyetherketoneketone (PEKK), a thermoplastic polymer in the polyaryletherketone (PAEK) family, other thermoplastic polymer(s), other thermoplastic material(s), zirconium, zirconia, ZTA (zirconia toughen alumina), silicon, other ceramic material(s), etc.

In this exemplary embodiment, the piezoelectric coating comprises piezoelectric poled PVDF dipped coating. Alternative processes besides dip coating may be used for providing the piezoelectric coating along the base and/or other materials besides PVDF may be used for the piezoelectric coating.

FIGS. 45-54 illustrate a piezoelectric implant (e.g., for use as a spinal fusion implant, etc.) according to an exemplary embodiment. In this exemplary embodiment, the piezoelectric implant includes a base (e.g., PEEK or other suitable material, etc.), piezoelectric elements (e.g., pre-poled piezoelectric PVDF inserts, etc.), and an electrically-conductive coating or shell encapsulation (e.g., a titanium or other electrically-conductive coating provided via sputtering, plasma spraying, sol-gel, physical vapor deposition process, or other suitable process, etc.). The electrically-conductive coating may be configured such that an entire outside of the piezoelectric implant has a negative charge. The piezoelectric elements may be bonded to the base with electrically non-conductive or dielectric adhesive.

In this exemplary embodiment, the base comprises polyetheretherketone (PEEK). But other suitable materials may also be used for the base, such as polyetherketoneketone (PEKK), a thermoplastic polymer in the polyaryletherketone (PAEK) family, other thermoplastic polymer(s), other thermoplastic material(s), zirconium, zirconia, ZTA (zirconia toughen alumina), silicon, other ceramic material(s), etc.

In this exemplary embodiment, the piezoelectric elements comprise polyvinylidene fluoride (PVDF) inserts poled to be piezoelectric. The PEEK base is between the piezoelectric inserts as shown in FIG. 52, such that the piezoelectric inserts' negative sides face outward and positive sides face inward. The piezoelectric inserts define protruding portions or ridges where compression occurs. Other materials besides PVDF may be used for the piezoelectric elements. For example, the piezoelectric elements may comprise potassium sodium niobate (KNN) poled to be piezoelectric. Or, for example, the piezoelectric elements may comprise polylactide (Poly(lactic acid), PLA) (e.g., PLLA, PDLA, PDLLA, etc.) poled to be piezoelectric.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. In addition, advantages and improvements that may be achieved with one or more exemplary embodiments of the present disclosure are provided for purpose of illustration only and do not limit the scope of the present disclosure, as exemplary embodiments disclosed herein may provide all or none of the above mentioned advantages and improvements and still fall within the scope of the present disclosure.

Specific dimensions, specific materials, and/or specific shapes disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. For example, when permissive phrases, such as "may comprise", "may include", and the like, are used herein, at least one embodiment comprises or includes the feature(s). As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected, or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The term "about" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. For example, the terms "generally", "about", and "substantially" may be used herein to mean within manufacturing tolerances. Or for example, the term "about" as used herein when modifying a quantity of an ingredient or reactant of the invention or employed refers to variation in the numerical quantity that can happen through typical measuring and handling procedures used, for example, when making concentrates or solutions in the real world through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", equivalents to the quantities are included.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A compounded material for a piezoelectric implant, the compounded material comprising barium titanate, wherein the piezoelectric implant is formed from the compounded material to include a first poled surface electrically connectable to an electrode and an opposite second poled surface electrically insulated to thereby maintain a single-polarity piezoelectric signal path during cyclic loading without shorting to an opposite polarity.

2. The compounded material of claim 1, wherein the compounded material comprises the barium titanate and polyetheretherketone.

3. The compounded material of claim 2, wherein the compounded material comprises a homogeneous compounded blend of the polyetheretherketone and the barium titanate.

4. The compounded material of claim 1, wherein the compounded material comprises the barium titanate and at least one other material including a thermoplastic material or ceramic material.

5. The compounded material of claim 1, wherein the compounded material comprises the barium titanate and at least one other material including one or more of polyetheretherketone (PEEK), polyetherketoneketone (PEKK), or a thermoplastic polymer.

6. The compounded material of claim 1, wherein:
the compounded material includes about 33.5 percent by volume of the barium titanate; or
the compounded material includes about 70 percent by weight of the barium titanate.

7. The compounded material of claim 1, wherein the compounded material includes a top surface and a bottom surface and is configured to have a single negative or positive polarity charge along either or both of the top and bottom surfaces.

8. The compounded material of claim 1, wherein:
the compounded material includes a top surface, a bottom surface, and at least one tunnel having an open end in one of the top surface or the bottom surface and extending from the one of said top surface or said bottom surface towards the other one of said top surface or said bottom surface;
the at least one tunnel does not extend completely through the other one of said top surface or said bottom surface such that the at least one tunnel has a closed end adjacent the other one of said top surface or said bottom surface; and
the compounded material is configured to have a single negative or positive polarity charge along either or both of the top and bottom surfaces.

9. The compounded material of claim 8, wherein:
the compounded material includes first and second corners diagonally opposite each other and third and fourth corners diagonally opposite each other;
the at least one tunnel includes first, second, third, and fourth tunnels respectively adjacent the first, second, third, and fourth corners of the compounded material;
each of the first and second tunnels starts at an opening defined in the top surface and extends downwardly from the top surface towards the bottom surface, the first and second tunnels do not extend completely through the bottom surface such that each of the first and second tunnels has a closed end adjacent the bottom surface; and
each of the third and fourth tunnels starts at an opening defined in the bottom surface and extends upwardly from the bottom surface towards the top surface, the third and fourth tunnels do not extend completely through the top surface such that each of the third and fourth tunnels has a closed end adjacent the top surface.

10. The compounded material of claim 1, wherein after the compounded material is poled at a temperature less than the Curie temperature of the barium titanate, the poled compounded material is piezoelectric.

11. The compounded material of claim 1, wherein after the compounded material is poled at room temperature within a range from about 20° C. to 22° C., the poled compounded material is piezoelectric.

12. The compounded material of claim 1, wherein the compounded material has a piezoelectric modulus or piezoelectric coefficient (D33) within a range from 4 to 33 or from 5 to 23.

13. The compounded material of claim 1, wherein the compounded material consists only of polyetheretherketone and the barium titanate.

14. The compounded material of claim 1, further comprising a film, sheet, or layer of material that has been poled to be piezoelectric and that is bonded to a surface of the compounded material, wherein the film, sheet, or layer of material comprises polyvinylidene fluoride (PVDF), potassium sodium niobate (KNN), or polylactide (Poly(lactic acid) PLA) including one or more of PLLA, PDLA, or PDLLA, and wherein only one side of the film, sheet, or layer of material poled to be piezoelectric is in electrical communication with the electrode, and an electrically nonconductive adhesive resides on an opposite side of the film, sheet, or layer of material poled to be piezoelectric.

15. A piezoelectric implant comprising the compounded material of claim 1, wherein the piezoelectric implant includes:
a piezoelectric body having at least one poled region defining a first poled surface and a second poled surface; and
an electrically conductive electrode coating along at least one bone-contacting surface of the piezoelectric implant;
wherein:
the electrically conductive electrode coating is electrically connected to the first poled surface of the piezoelectric body to receive a piezoelectric electrical signal generated under mechanical strain;
the second poled surface is electrically insulated from the electrically conductive electrode coating by a non-conductive material or structural barrier such that, under cyclic strain, a time-varying piezoelectric signal of a single polarity is conducted over the electrically conductive electrode coating without shorting to an opposite polarity; and
the electrically conductive electrode coating forms an electrode path over the at least one bone-contacting surface of the piezoelectric implant for distributing the piezoelectric signal to promote bone growth.

16. A material for a piezoelectric implant comprising one or more of:
ceramic material doped with barium titanate;
polylactide (Poly(lactic acid), PLA) poled to be piezoelectric;

polyvinylidene fluoride (PVDF) poled to be piezoelectric; or potassium sodium niobate (KNN) poled to be piezoelectric;

wherein the material is configured such that only a first poled surface of the material is electrically connectable to an electrode, and an opposite second poled surface of the material is electrically insulated to maintain a single-polarity piezoelectric signal path during cyclic loading without shorting to an opposite polarity.

17. The material of claim 16, wherein;

the material comprises a film, sheet, or layer of the polyvinylidene fluoride (PVDF) poled to piezoelectric; and only one side of the film, sheet, or layer of the polyvinylidene fluoride (PVDF) is in electrical communication with the electrode, and an electrically non-conductive adhesive resides on an opposite side of the film, sheet, or layer of the polyvinylidene fluoride (PVDF).

18. The material of claim 16, wherein:

the material comprises a film, sheet, or layer of the potassium sodium niobate (KNN) poled to be piezoelectric; and only one side of the film, sheet, or layer of the potassium sodium niobate (KNN) is in electrical communication with the electrode, and an electrically non-conductive adhesive resides on an opposite side of the film, sheet, or layer of the potassium sodium niobate (KNN).

19. A piezoelectric implant comprising:

a piezoelectric body having at least one poled region defining a first poled surface and a second poled surface; and an electrically conductive electrode coating along at least one bone-contacting surface of the piezoelectric implant;

wherein:

the electrically conductive electrode coating is electrically connected to the first poled surface of the piezoelectric body to receive a piezoelectric electrical signal generated under mechanical strain;

the second poled surface is electrically insulated from the electrically conductive electrode coating by a non-conductive material or structural barrier such that, under cyclic strain, a time-varying piezoelectric signal of a single polarity is conducted over the electrically conductive electrode coating without shorting to an opposite polarity; and the electrically conductive electrode coating forms an electrode path over the at least one bone-contacting surface of the piezoelectric implant for distributing the piezoelectric signal to promote bone growth.

20. The piezoelectric implant of claim 19, wherein:

the electrically conductive electrode coating comprises an electrically conductive titanium electrode coating deposited by sputtering, plasma spraying, sol-gel processing, or physical vapor deposition along the at least one bone-contacting surface of the piezoelectric implant; or the piezoelectric implant further comprises titanium or other electrode coating fully encapsulating the piezoelectric implant such that an entire outside of the piezoelectric implant has a single-polarity positive or negative charge during cyclic loading without shorting to an opposite polarity.

* * * * *